(12) United States Patent
Xia et al.

(10) Patent No.: US 10,532,357 B1
(45) Date of Patent: Jan. 14, 2020

(54) SINGLE-SHEATH MICROFLUIDIC CHIP

(71) Applicant: Genus plc, DeForest, WI (US)

(72) Inventors: Zheng Xia, DeForest, WI (US); Gopakumar Kamalakshakurup, DeForest, WI (US)

(73) Assignee: GENUS PLC, DeForest, WI (US)

( * ) Notice: Subject to any disclaimer, the term of this patent is extended or adjusted under 35 U.S.C. 154(b) by 0 days.

(21) Appl. No.: 16/396,138

(22) Filed: Apr. 26, 2019

(51) Int. Cl.
| | |
|---|---|
| *B01L 3/00* | (2006.01) |
| *G01N 35/00* | (2006.01) |
| *G01N 33/48* | (2006.01) |
| *G01N 15/06* | (2006.01) |
| *G01N 15/14* | (2006.01) |
| *B65G 51/00* | (2006.01) |

(52) U.S. Cl.
CPC .... B01L 3/502776 (2013.01); G01N 15/1404 (2013.01); G01N 15/1484 (2013.01); *B01L 2200/0636* (2013.01); *B01L 2400/0487* (2013.01); *B65G 51/00* (2013.01); *G01N 2015/1409* (2013.01)

(58) Field of Classification Search
CPC ..... B01L 3/00; B01L 3/502776; G01N 35/00; G01N 33/48; G01N 15/06; G01N 33/00; G01N 15/1404
USPC ..... 422/502, 503, 504; 436/43, 63, 174, 180
See application file for complete search history.

(56) References Cited

U.S. PATENT DOCUMENTS

| | | | |
|---|---|---|---|
| 7,311,476 B2 | 12/2007 | Gilbert et al. | |
| 7,611,309 B2 | 11/2009 | Gilbert et al. | |
| 8,529,161 B2 | 9/2013 | Gilbert et al. | |
| 9,446,912 B2 | 9/2016 | Gilbert et al. | |
| 2005/0123450 A1* | 6/2005 | Gilbert | B01L 3/502776 422/81 |
| 2006/0078888 A1* | 4/2006 | Griffiths | B01F 3/0807 435/6.11 |
| 2011/0263747 A1* | 10/2011 | Doyle | G01N 33/54313 522/33 |
| 2013/0295602 A1* | 11/2013 | Fowler | C12Q 1/686 435/34 |
| 2014/0273192 A1* | 9/2014 | Sharpe | B01L 3/502761 435/288.7 |
| 2014/0318645 A1* | 10/2014 | Koksal | F17D 1/08 137/559 |

\* cited by examiner

*Primary Examiner* — Brian J. Sines
(74) *Attorney, Agent, or Firm* — Nguyen Tarbet

(57) ABSTRACT

Microfluidic devices and methods for focusing components in a fluid sample are described herein. The microfluidic device has at least one flow focusing channel where the components are focused or re-oriented by the geometry of the channel. From an upstream end of the flow focusing channel to a downstream end of the flow focusing channel, at least a portion of the flow focusing channel has a reduction in height and at least a portion of the flow focusing channel narrows in width, thereby geometrically constricting the flow focusing channel. The devices and methods can be utilized in sex-sorting of sperm cells to improve performance and increase eligibility.

5 Claims, 16 Drawing Sheets

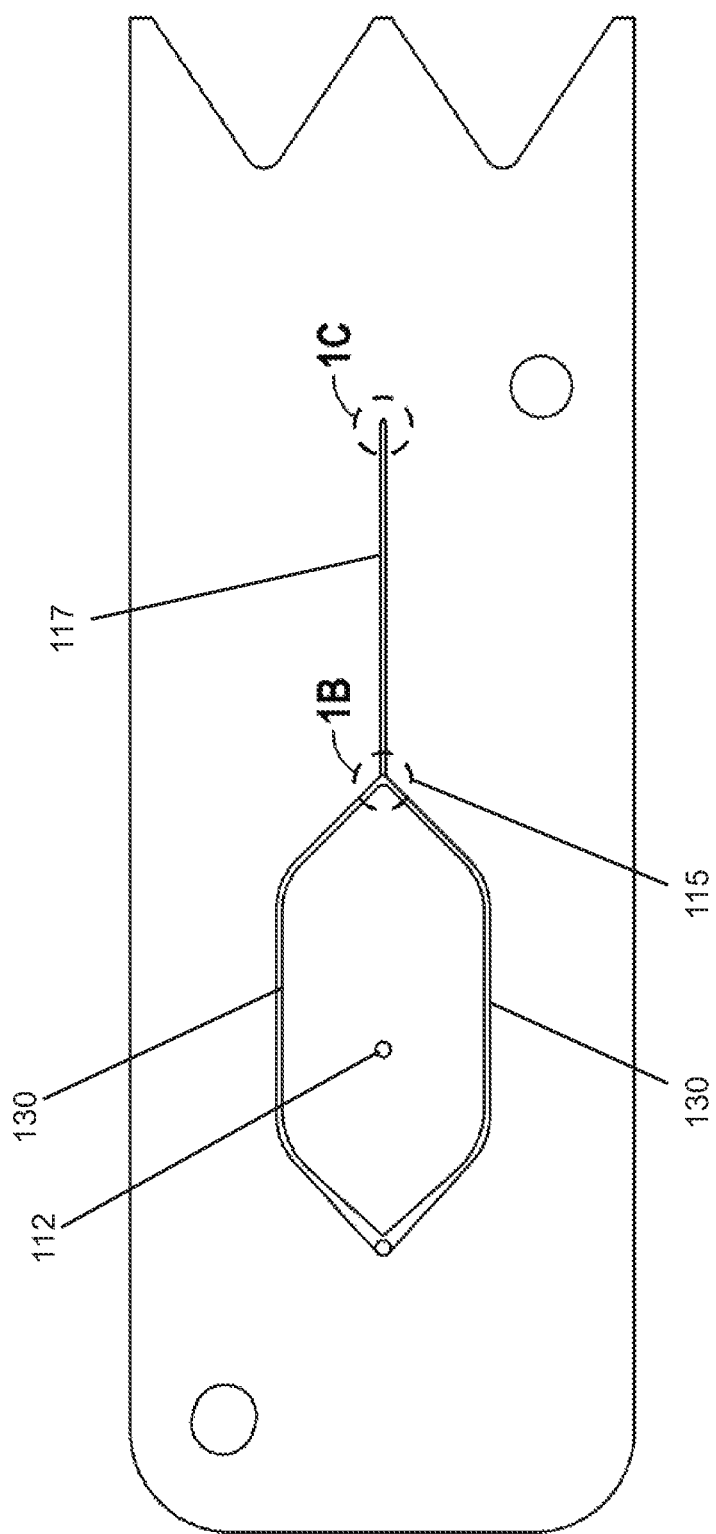

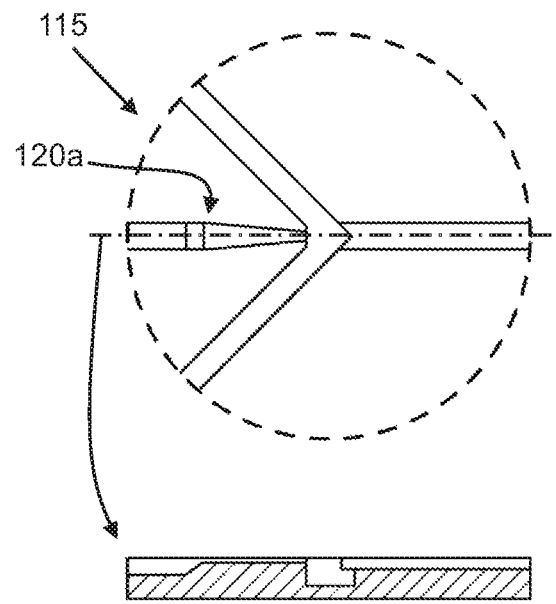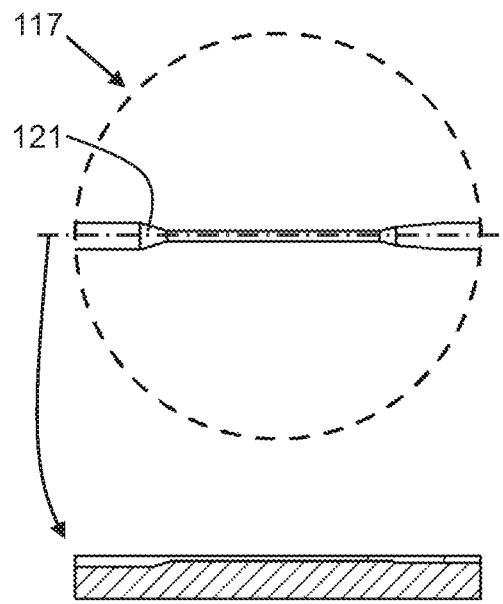
FIG. 2B        FIG. 2C
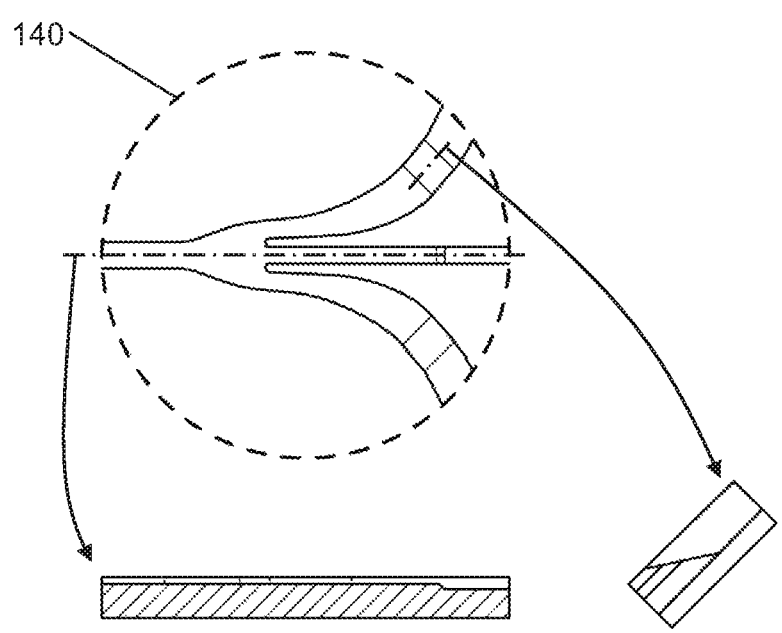
FIG. 2D

SINGLE-SHEATH MICROFLUIDIC CHIP

BACKGROUND OF THE INVENTION

Field of the Invention

The present invention relates to a microfluidic chip design, in particular, to a microfluidic chip for isolating particles or cellular materials using laminar flow from a single sheath and geometric focusing.

Background Art

Microfluidics enables the use of small volumes for preparing and processing samples, such as various particles or cellular materials. When separating a sample, such as the separation of sperm into viable and motile sperm from non-viable or non-motile sperm, or separation by gender, the process is often a time-consuming task and can have severe volume restrictions. Current separation techniques cannot, for example, produce the desired yield, or process volumes of cellular materials in a timely fashion. Furthermore, existing microfluidic devices do not effectively focus or orient the sperm cells.

Hence, there is need for a microfluidic device and separation process utilizing said device that is continuous, has high throughput, provides time saving, and causes negligible or minimal damage to the various components of the separation. In addition, such a device and method can have further applicability to biological and medical areas, not just in sperm sorting, but in the separation of blood and other cellular materials, including viral, cell organelle, globular structures, colloidal suspensions, and other biological materials.

BRIEF SUMMARY OF THE INVENTION

It is an objective of the present invention to provide microfluidic devices and methods that allow for focusing and orienting particles or cellular materials, as specified in the independent claims. Embodiments of the invention are given in the dependent claims. Embodiments of the present invention can be freely combined with each other if they are not mutually exclusive.

In some aspects, the present invention features microfluidic devices for use in sperm cell sexing and trait enrichment. The microfluidic device may comprise at least one flow focusing channel where the components are focused or re-oriented by the geometry of the channel. From an upstream end of the flow focusing channel to a downstream end of the flow focusing channel, at least a portion of the flow focusing channel has a reduction in height and at least a portion of the flow focusing channel narrows in width, thereby geometrically constricting the flow focusing channel.

One of the unique and inventive technical features of the present invention is the physical restriction of the channel geometry at the flow focusing region. Without wishing to limit the invention to any theory or mechanism, it is believed that the technical feature of the present invention advantageously eliminates the second sheath flow structure from the microfluidic device such that the use of a secondary sheath fluid to focus/orient sperm cells becomes unnecessary, thus reducing the volume of sheath fluid used as compared to existing devices that have two focusing regions using sheath fluids for stream compression. This provides an additional benefit of reducing operational costs for equipment and supplies, and further simplifying system complexity. None of the presently known prior references or work has the unique inventive technical feature of the present invention.

The inventive technical feature of the present invention surprisingly resulted in equivalent purity, better performance, and improved functionality for Y-skewed sperm cells as compared to the prior devices having two focusing regions using sheath fluids. For instance, the microfluidic device of the present invention unexpectedly improved the orientation of the sperm cells, which is believed to have increased the eligibility, i.e. higher number of cells detected, sorted, and ablated. In addition, the device of the present invention was able to enhance resolution between the Y-chromosome bearing sperm cells and the X-chromosome bearing sperm cells, which resulted in effective discrimination of Y-chromosome-bearing sperm cells.

Further still, the prior references teach away from the present invention. For example, contrary to the present invention, U.S. Pat. No. 7,311,476 teaches the use of sheath fluids to focus a fluid stream in its disclosure of microfluidic chips that have a first focusing region and a second focusing region downstream of the first, where each region introduces sheath fluids to focus the sheath fluid around particles, and that the second (downstream) focusing region requires the introduction of additional sheath fluid to achieve the necessary focusing.

In some embodiments, the microfluidic chip includes a plurality of layers in which are disposed a plurality of channels including: a sample input channel into which a sample fluid mixture of components to be isolated is inputted, and two focusing regions comprising a first focusing region that focuses particles in the sample fluid and a second focusing region that focuses particles in the sample fluid, where one of the focusing regions includes introduction of a sheath fluid via one or more sheath fluid channels, and the other focusing region includes geometric compression without introducing additional sheath fluid. Geometric compression refers to physical restriction due to a narrowing in size of the sample channel in both the vertical and horizontal axes (i.e. from above and below and from both the left and right sides, relative to the direction of travel along the sample channel). In some aspects, the first focusing region may combine geometric with the sheath fluid introduction; however, the second focusing region does not utilize additional sheath fluid for stream focusing or particle orienting. In other aspects, the microfluidic chip can be loaded on a microfluidic chip cassette which is mounted on a microfluidic chip holder.

In some embodiments, the sample input channel and the one or more sheath channels are disposed in one or more planes of the microfluidic chip. For instance, a sheath channel may be disposed in a different plane than a plane in which the sample input channel is disposed. In other embodiments, the sample input channel and the sheath channels are disposed in one or more structural layers, or in-between structural layers of the microfluidic chip. As an example, the one or more sheath channels may be disposed in a different structural layer than a structural layer in which the sample input channel is disposed.

In one embodiment, the sample input channel may taper at an entry point into the intersection region with the sheath channel. In another embodiment, the sheath channel may taper at entry points into the intersection region with the sample input channel. In some embodiments, the microfluidic device may include one or more output channels fluidly coupled to the sample channel. The one or more output channels may each have an output disposed at its end. In other embodiments, the microfluidic chip may further include one or more notches disposed at a bottom edge of the microfluidic chip to isolate the outputs of the output channels.

In some embodiments, the microfluidic chip system includes an interrogation apparatus which interrogates and identifies the components of the sample fluid mixture in the sample input channel, in an interrogation chamber disposed downstream from the flow focusing region. In one embodiment, the interrogation apparatus includes a radiation source configured to emit a beam to illuminate and excite the components in said sample fluid mixture. The emitted light induced by the beam is received by an objective lens. In another embodiment, the interrogation apparatus may comprise a detector such as a photomultiplier tube (PMT), an avalanche photodiode (APD), or a silicon photomultiplier (SiPM).

In some embodiments, the microfluidic chip includes a sorting mechanism which sorts said components in said sample fluid mixture downstream from said interrogation chamber, by selectively acting on individual components in said sample fluid mixture. In one embodiment, the sorting mechanism may comprise a laser kill/ablation. Other examples of sorting mechanisms that may be used in accordance with the present invention include, but are not limited to, particle deflection/electrostatic manipulation, droplet sorting/deflection, mechanical sorting, fluid switching, piezoelectric actuation, optical manipulation (optical trapping, holographic steering, and photonic/radiation pressure), surface acoustic wave (SAW) deflection, electrophoresis/electrical disruption, micro-cavitation (laser induced, electrically induced). In some embodiments, the isolated components are moved into one of the output channels, and unselected components flow out through another output channel.

In further embodiments, the microfluidic chip may be operatively coupled to a computer which controls the pumping of one of the sample fluid mixture or the sheath fluid into the microfluidic chip. In another embodiment, the computer can display the components in a field of view acquired by a CCD camera disposed over the interrogation window in the microfluidic chip.

In some embodiments, the cells to be isolated may include at least one of viable and motile sperm from non-viable or non-motile sperm; sperm isolated by gender and other sex sorting variations; stem cells isolated from cells in a population; one or more labeled cells isolated from unlabeled cells including sperm cells; cells, including sperm cells, distinguished by desirable or undesirable traits; genes isolated in nuclear DNA according to a specified characteristic; cells isolated based on surface markers; cells isolated based on membrane integrity or viability; cells isolated based on potential or predicted reproductive status; cells isolated based on an ability to survive freezing; healthy cells isolated from contaminants or debris; healthy cells isolated from damaged cells; red blood cells isolated from white blood cells and platelets in a plasma mixture; or any cells isolated from any other cellular components into corresponding fractions.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1A shows a bottom view of a top layer of a microfluidic device according to one embodiment of the present invention.

FIG. 2B shows a close-up view and a cross-sectional side view of the intersection region in the bottom layer shown in FIG. 2A.

FIG. 2C shows a close-up view and a cross-sectional side view of the flow focusing region in the bottom layer shown in FIG. 2A.

FIG. 2D shows a close-up view and a cross-sectional side view of an output channel region in the bottom layer shown in FIG. 2A.

FIGS. 4A-4F show multiple embodiments of the flow focusing region in the microfluidic device of the present invention, wherein each figure includes a top view, a side view, and various cross-sectional views of the flow focusing region. The multiple embodiments demonstrate geometric compression of the micro-channel by sequential raising of the bottom surface, lowering of the top surface, and side tapering in varying combinations.

Figure 5:
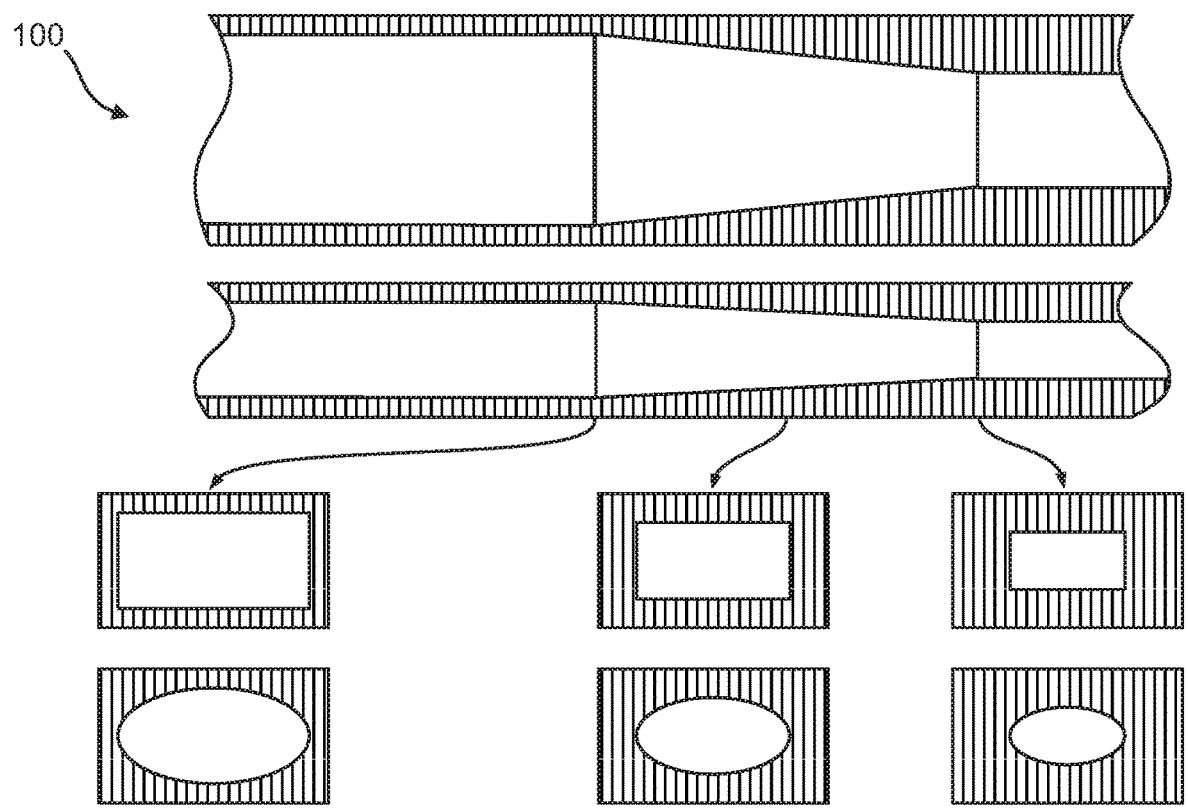

FIG. 5 shows an embodiment of the flow focusing region in the microfluidic device, including a top view, a side view, and various cross-sectional views of the flow focusing region. This embodiment demonstrates geometric compression of the micro-channel by simultaneously raising of the bottom surface, lowering of the top surface, and side tapering.

Figure 6A:
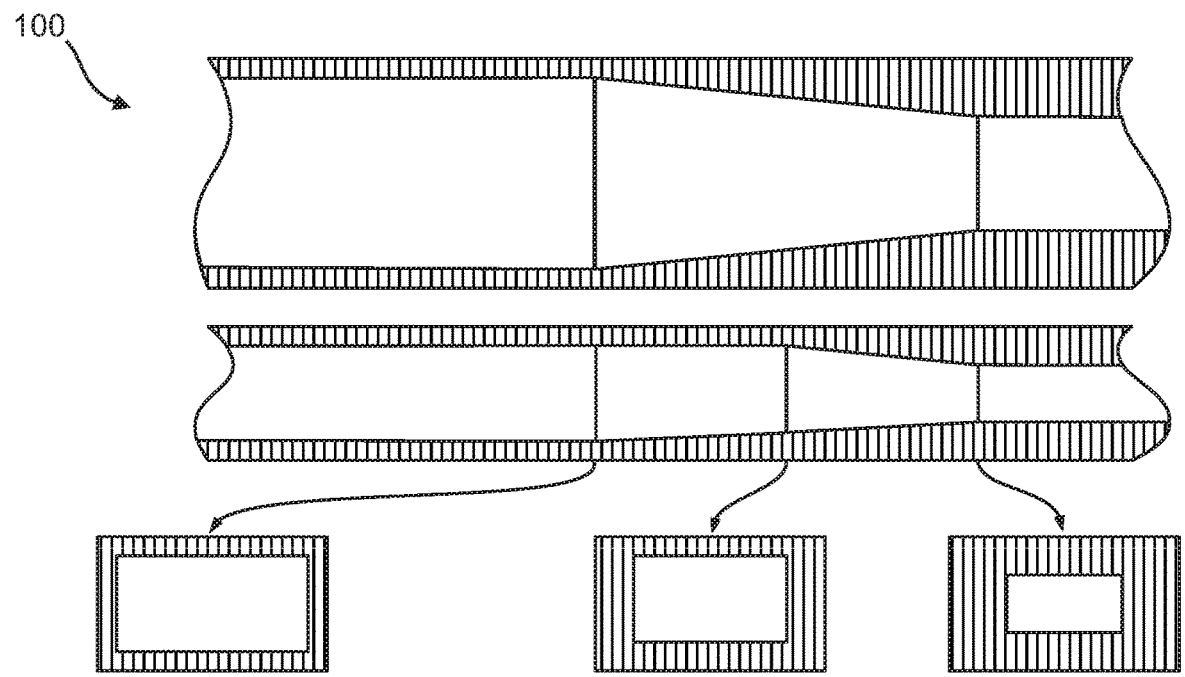
Figure 6B:
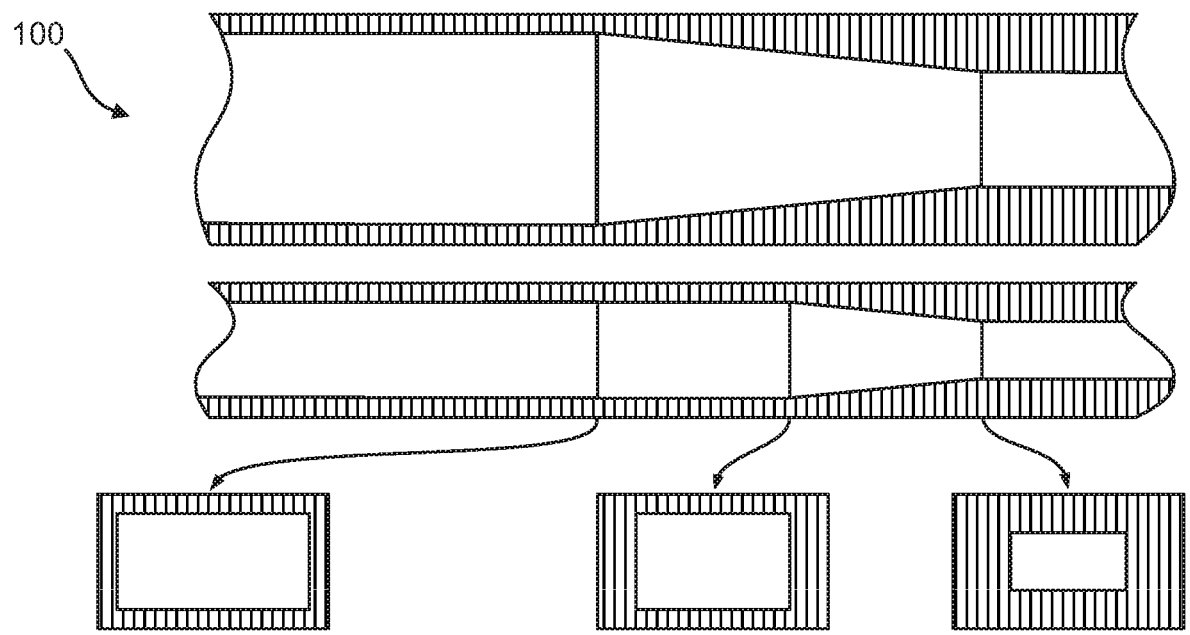
Figure 6C:
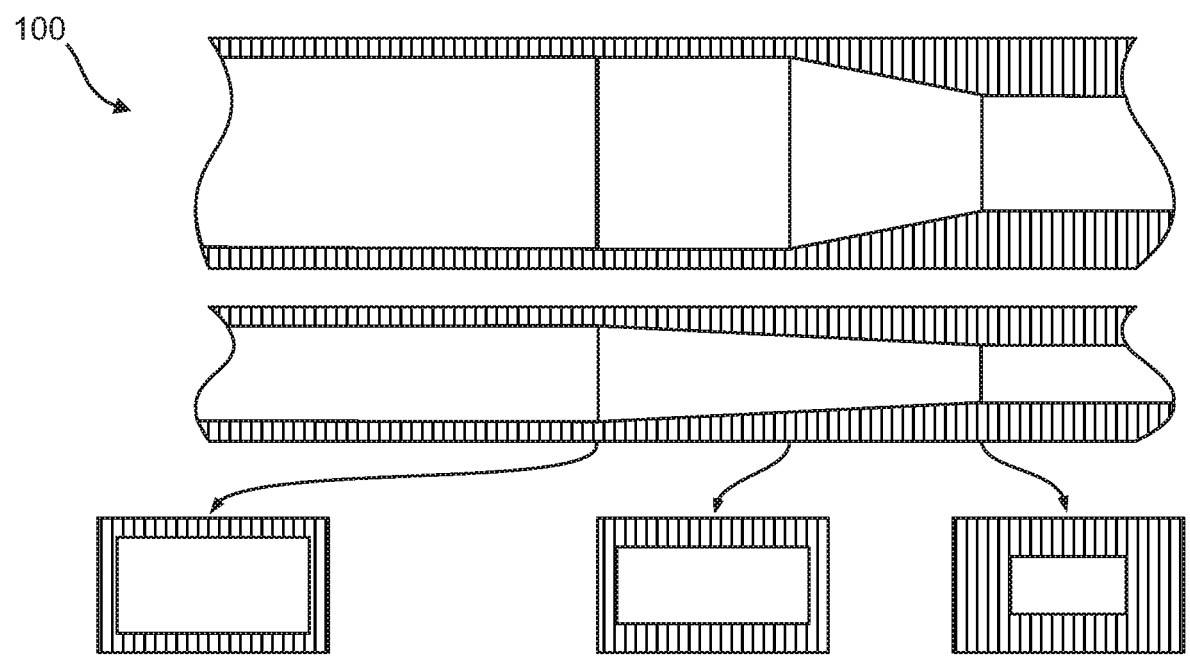

FIGS. 6A-6C show multiple embodiments of the flow focusing region in the microfluidic device of the present invention, wherein each figure includes a top view, a side view, and various cross-sectional views of the flow focusing region. The multiple embodiments demonstrate geometric compression of the micro-channel by simultaneous raising of the bottom surface and lowering of the top surface with an overlap of side tapering.

Figure 7A:
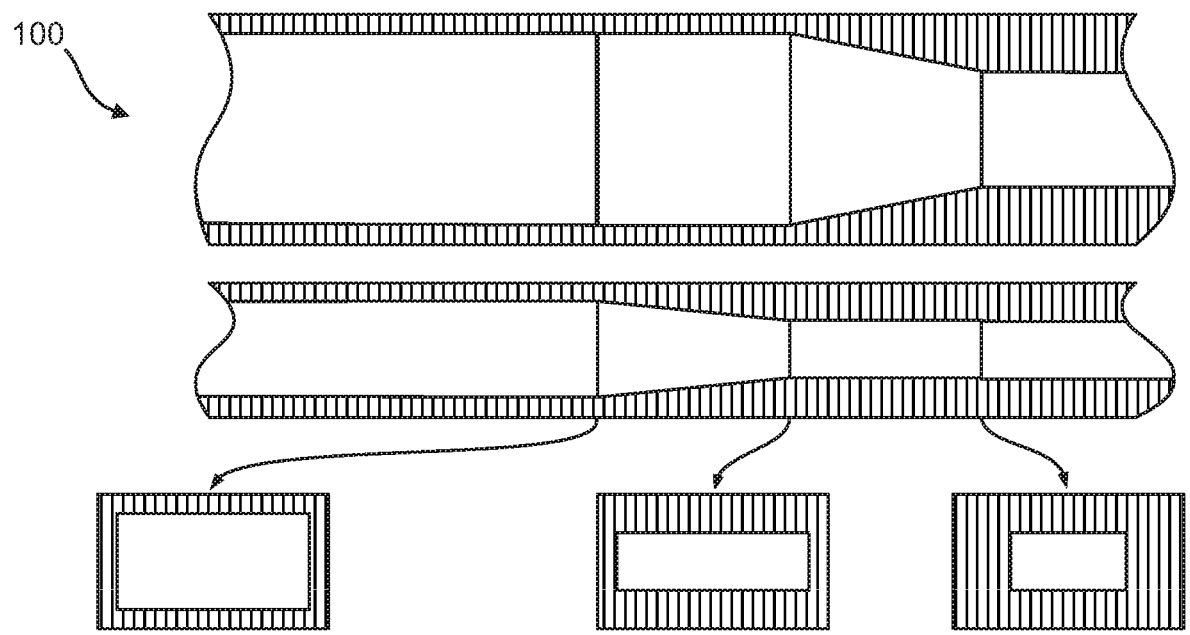
Figure 7B:
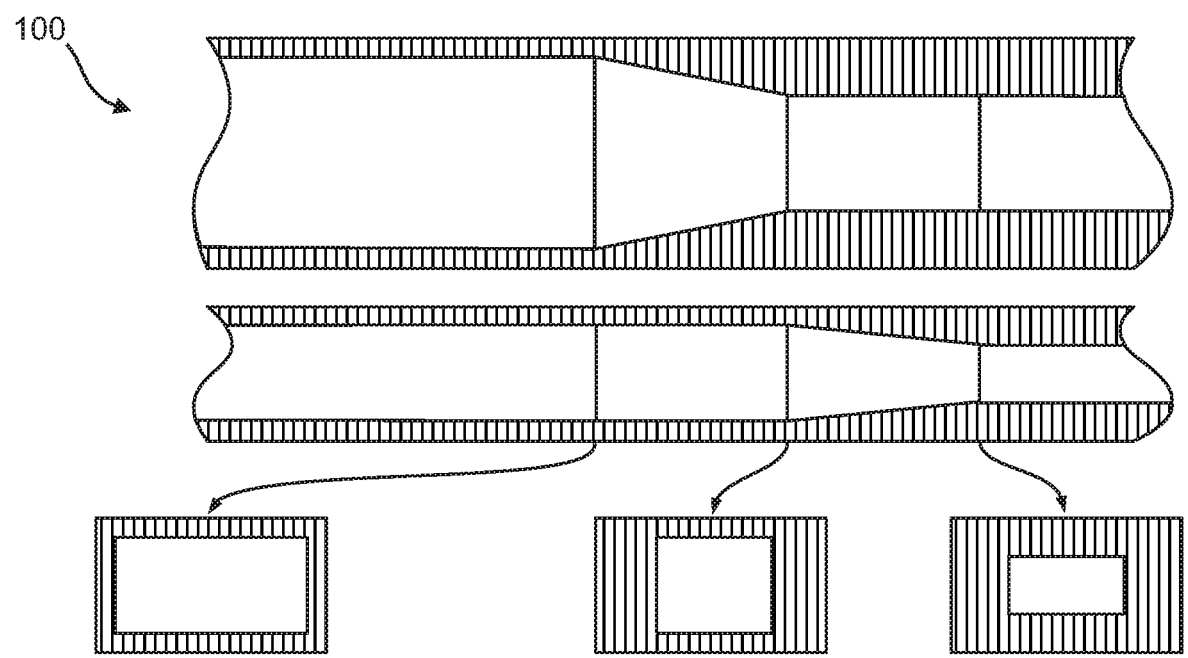

FIGS. 7A-7B show non-limiting embodiments of the flow focusing region in the microfluidic device, wherein each figure includes a top view, a side view, and various cross-sectional views of the flow focusing region. The embodiments demonstrate geometric compression of the micro-channel by simultaneous raising of the bottom surface and lowering of the top surface with sequential side tapering.

Figure 8A:
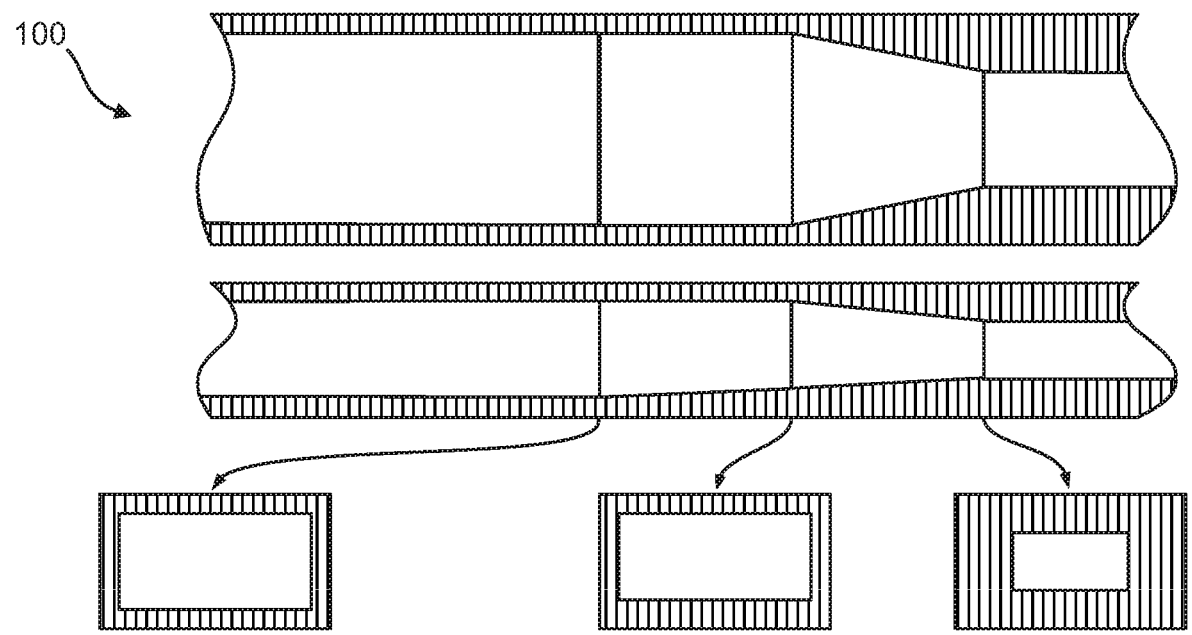
Figure 8B:
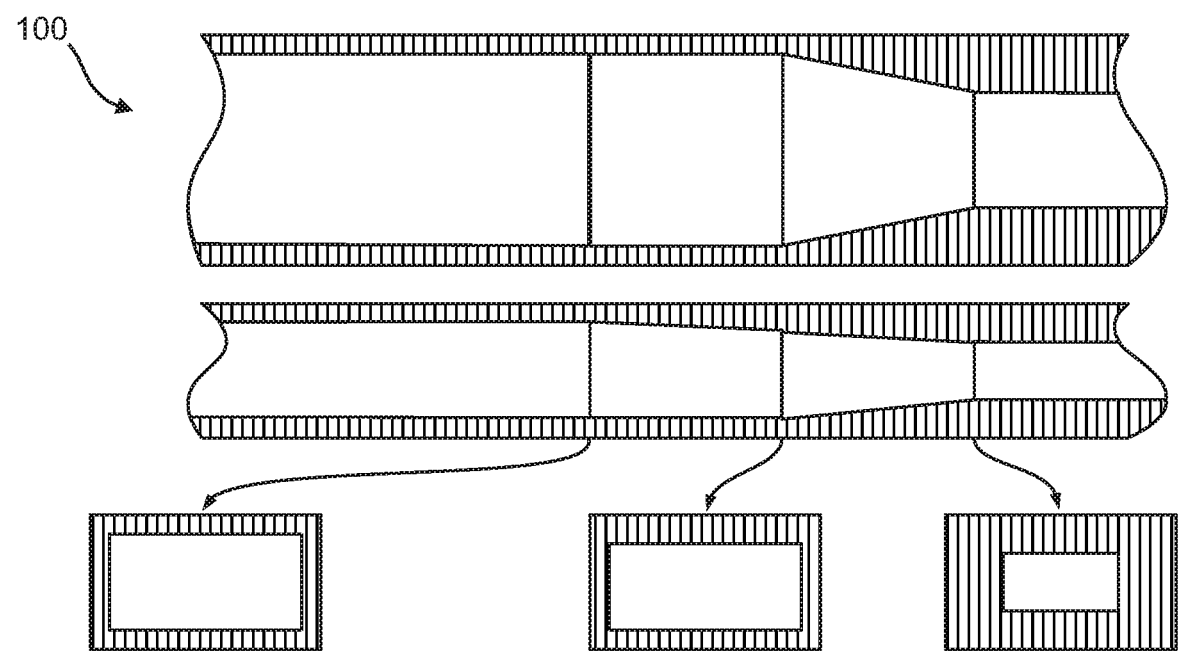

FIGS. 8A-8B show other non-limiting embodiments of the flow focusing region, wherein each figure includes a top view, a side view, and various cross-sectional views of the flow focusing region. The embodiments demonstrate geometric compression of the micro-channel by simultaneously compression of all four sides and an overlapping ramp on the bottom surface or top surface.

Figure 9A:
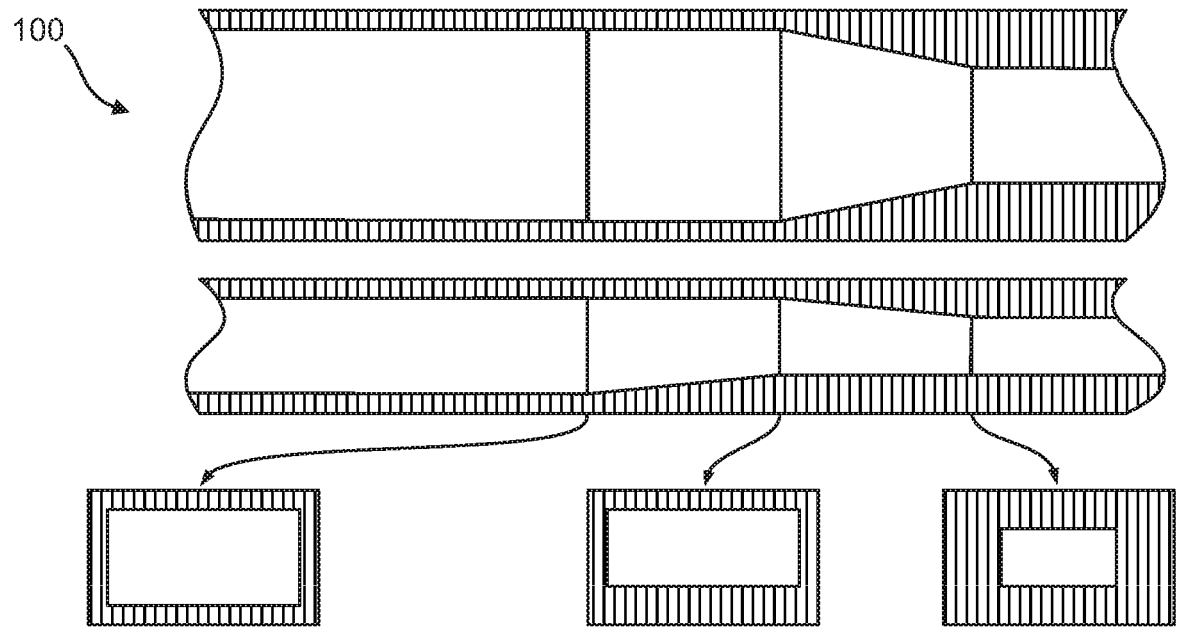
Figure 9B:
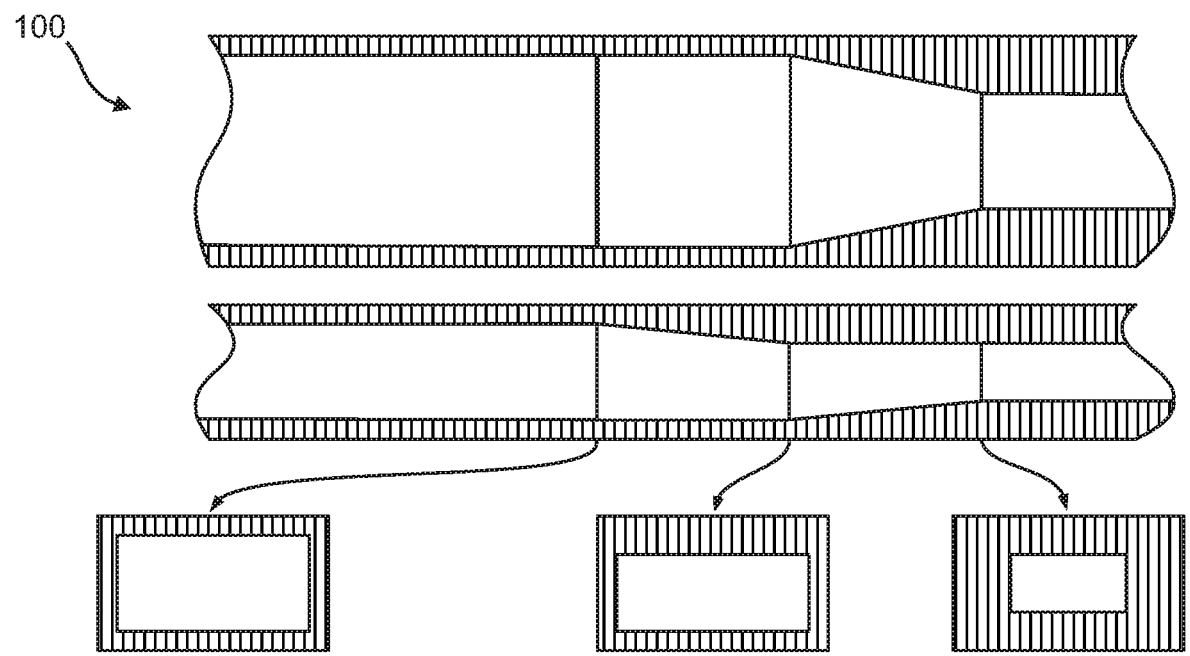

FIGS. 9A-9B show other non-limiting embodiments of the flow focusing region, wherein each figure includes a top view, a side view, and various cross-sectional views of the flow focusing region. The embodiments demonstrate geometric compression of the micro-channel by simultaneously compression of three sides and a sequential ramp on the bottom surface or top surface.

Figure 10A:
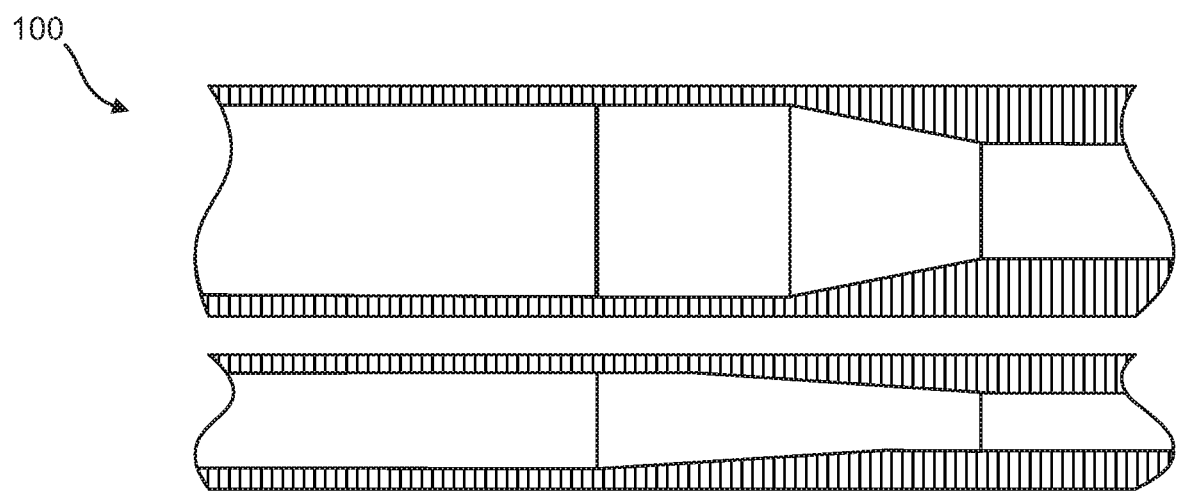
Figure 10B:
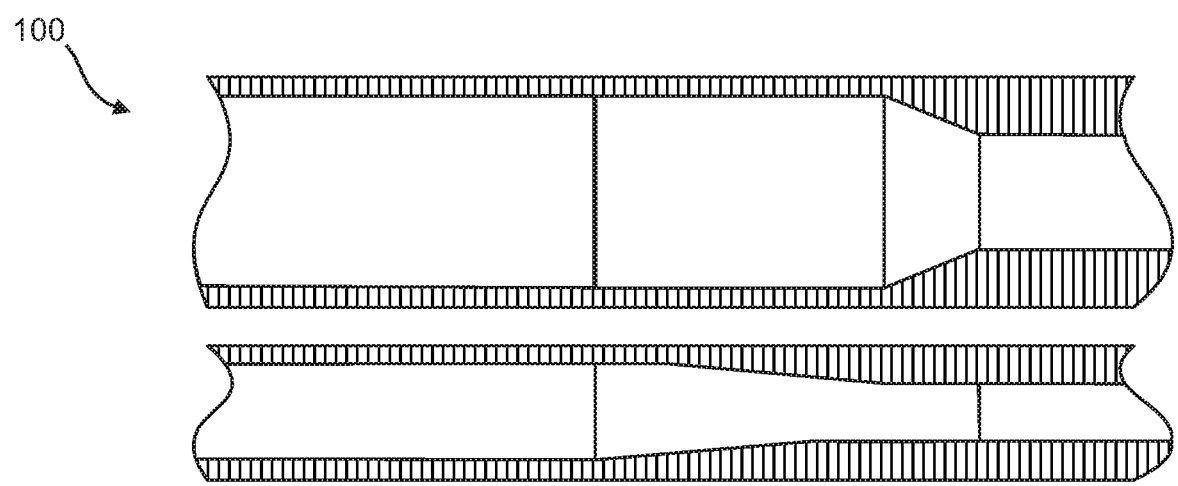

FIGS. 10A-10B show other non-limiting embodiments of the flow focusing region, wherein each figure includes a top view and a side view. The embodiments demonstrate geometric compression of the micro-channel by overlapping compression of four sides.

Figure 11:
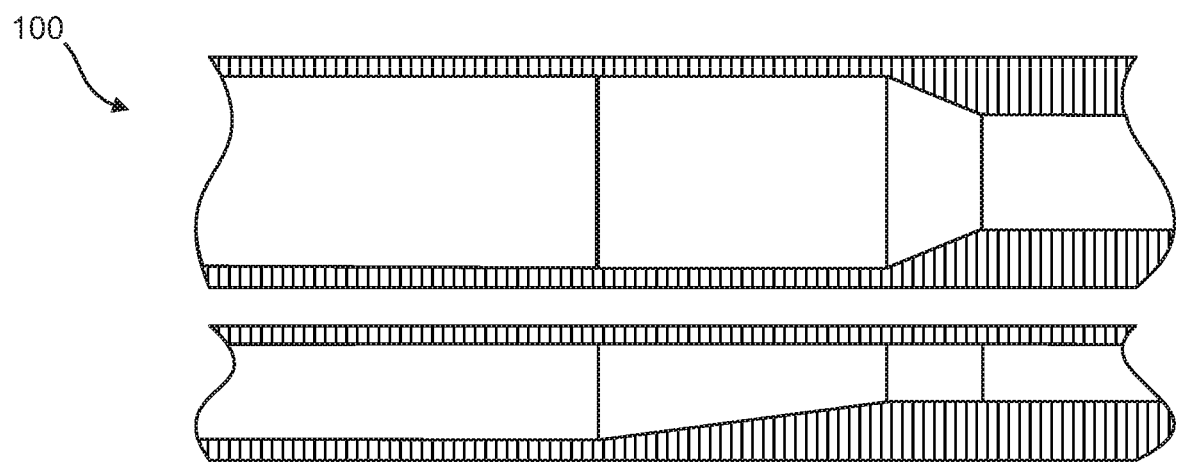

FIG. 11 shows a non-limiting embodiment of a top view and a side view of the flow focusing region. This embodiment demonstrates geometric compression of the micro-channel by sequential compression of only three sides.

Figure 12:
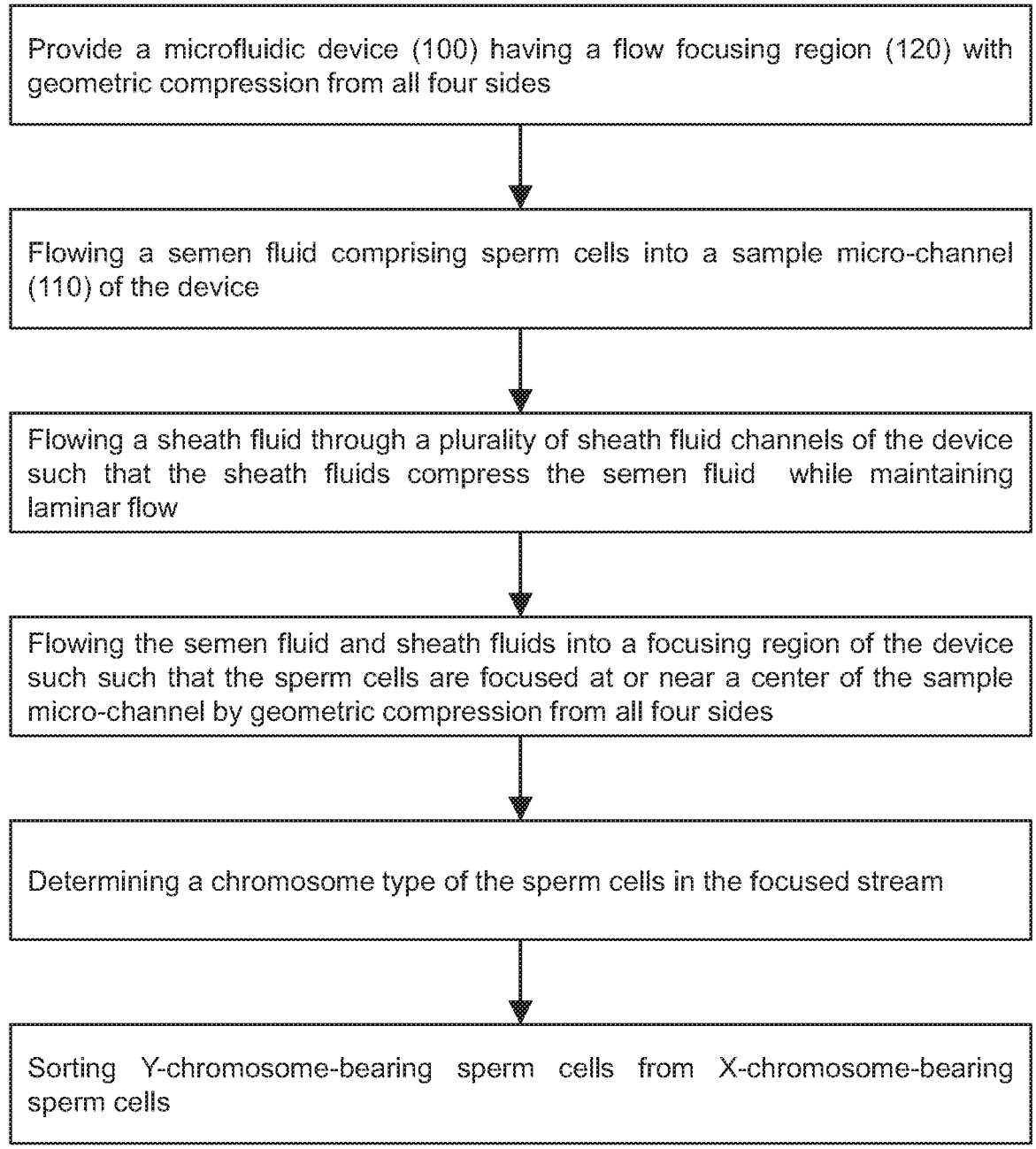

FIG. 12 is a non-limiting example of a flow diagram for a method of gender-skewing a semen fluid sample.

DETAILED DESCRIPTION OF THE INVENTION

Before turning to the figures, which illustrate the illustrative embodiments in detail, it should be understood that the present disclosure is not limited to the details or methodology set forth in the description or illustrated in the figures. It should also be understood that the terminology is for the purpose of description only and should not be regarded as limiting. An effort has been made to use the same or like reference numbers throughout the drawings to refer to the same or like parts.

Following is a list of elements corresponding to a particular element referred to herein:
100 microfluidic chip
110 first/sample micro-channel
112 micro-channel inlet
115 intersection region
120 flow focusing channel/region
121 bottom surface
122 top surface
123 bottom ramp
124 top ramp
125 first sidewall
126 second sidewall
127 upstream end of the flow focusing channel
128 downstream end of the flow focusing channel
129 cross-sectional area
130 sheath fluid micro-channel
140 output micro-channel
150 output notches In one aspect, the present disclosure relates to a microfluidic chip design and methods that can isolate particles or cellular materials, such as sperm and other particles or cells, into various components and fractions. For example, the various embodiments of the present invention provide for isolating components in a mixture, such as isolating viable and motile sperm from non-viable or non-motile sperm; isolating sperm by gender, and other sex sorting variations; isolating stems cells from cells in a population; isolating one or more labeled cells from un-labeled cells distinguishing desirable/undesirable traits; isolating genes in nuclear DNA according to a specified characteristic; isolating cells based on surface markers; isolating cells based on membrane integrity (viability), potential or predicted reproductive status (fertility), ability to survive freezing, etc.; isolating cells from contaminants or debris; isolating healthy cells from damaged cells (i.e., cancerous cells) (as in bone marrow extractions); red blood cells from white blood cells and platelets in a plasma mixture; and isolating any cells from any other cellular components, into corresponding fractions.

In other aspects, the various embodiments of the present invention provide systems and methods particularly suited for sorting sperm cells to produce a sexed semen product in which the live, progressively motile sperm cells are predominantly Y-chromosome bearing sperm cells. In some embodiments, the systems and methods of the present invention can produce a sex-sorted or gender skewed semen product comprising at least 55% of Y-chromosome bearing sperm cells. In other embodiments, the systems and methods can produce a sexed semen product comprising about 55% to about 90% of Y-chromosome bearing sperm cells. In yet other embodiments, the systems and methods can produce a sexed semen product comprising at least 90%, or at least 95%, or at least 99% of Y-chromosome bearing sperm cells.

While the description below focuses on the separation of sperm into viable and motile sperm from non-viable or non-motile sperm, or isolating sperm by gender and other sex sorting variations, or isolating one or more labeled cells from unlabeled cells distinguishing desirable/undesirable traits, etc., the present invention may be extended to other types of particulate, biological or cellular matter, which are capable of being interrogated by fluorescence techniques within a fluid flow, or which are capable of being manipulated between different fluid flows into different outputs.

The various embodiments of the microfluidics chip utilize one or more flow channels having substantially laminar flow, and a flow focusing region for focusing and/or orienting one or more components in the fluid, allowing the one or more components to be interrogated for identification and to be isolated into flows that exit into one or more outputs. In addition, the various components in the mixture may be subjected to one or more sorting processes on-chip using various sorting techniques, such as, for example, particle deflection/electrostatic manipulation; droplet sorting/deflection; mechanical sorting; fluid switching; piezoelectric actuation; optical manipulation (optical trapping, holographic steering, and photonic/radiation pressure); laser kill/ablation; surface acoustic wave (SAW) deflection; electrophoresis/electrical disruption; micro-cavitation (laser induced, electrically induced); or by magnetics (i.e., using magnetic beads). The various embodiments of the present invention thereby provide focusing and separation of components on a continuous basis without the potential damage and contamination of prior art methods, particularly as provided in sperm separation. The continuous process of the invention also provides significant time savings in isolating the fluid components.

Microfluidic Chip Assembly

Figure 1B:
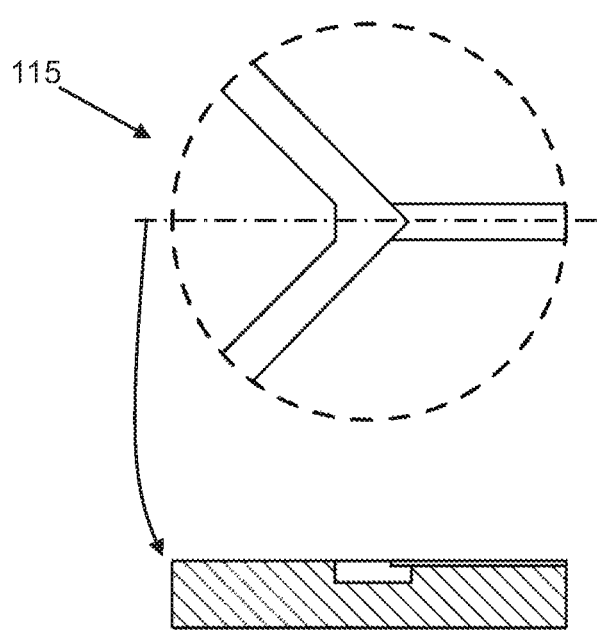
FIG. 1B shows a close-up view and a cross-sectional side view of an intersection region in the top layer shown in FIG. 1A.
Figure 1C:
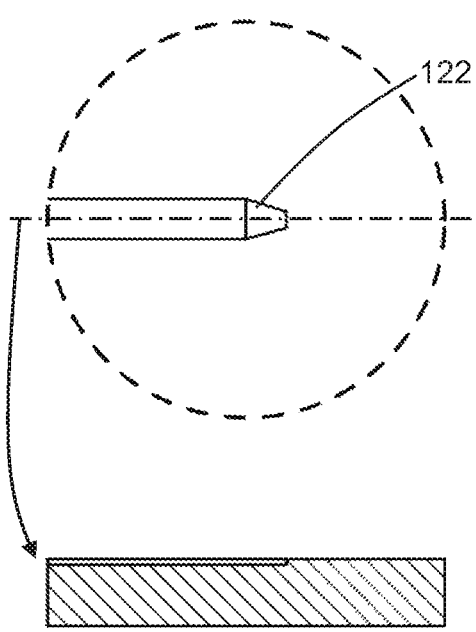
FIG. 1C shows a close-up view and a cross-sectional side view of a flow focusing region in the top layer shown in FIG. 1A.
Figure 2A:
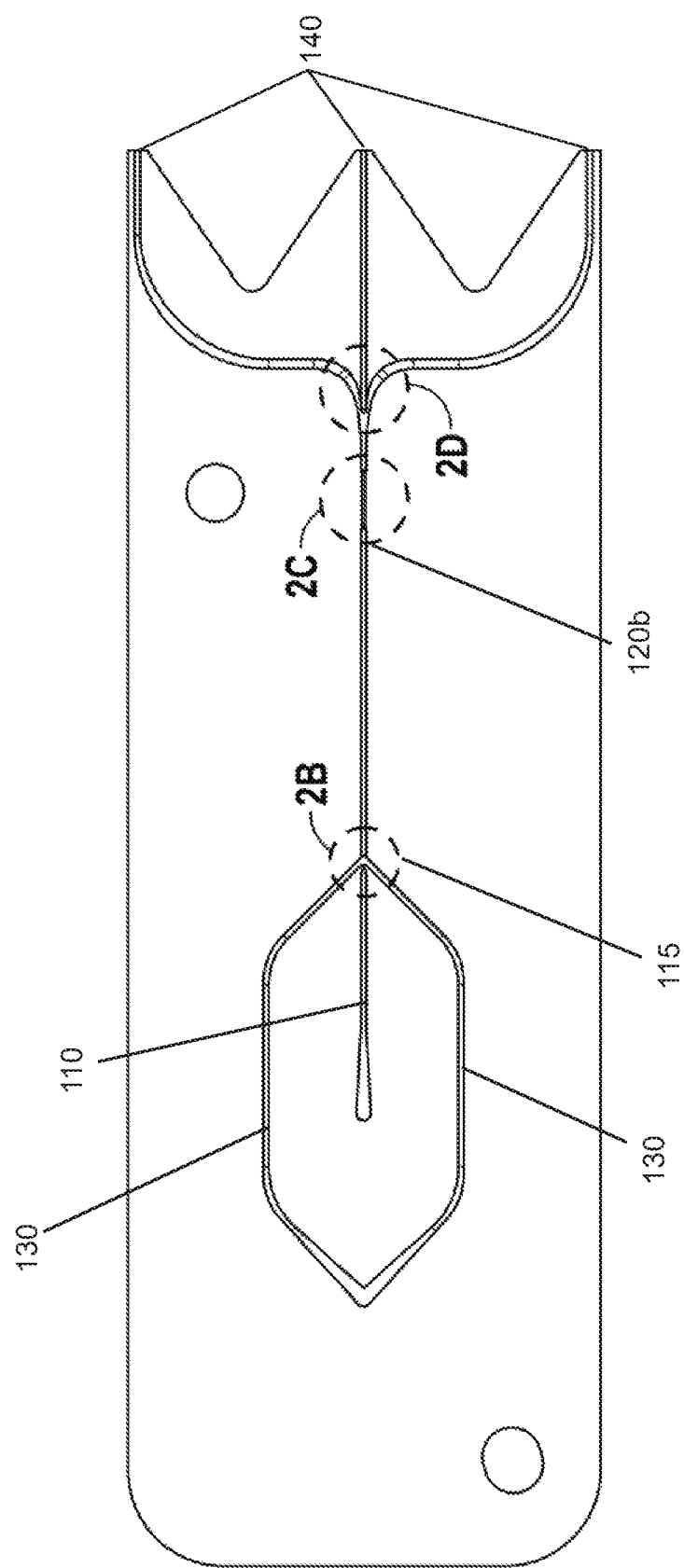
FIG. 2A shows a top view of a bottom layer of the microfluidic device.

FIGS. 1-3 show an illustrative embodiment of a microfluidic chip (100) of the present invention. The microfluidic chip may be manufactured of glass (e.g. soda lime, quartz, borosilicate, etc.) or a suitable thermoplastic (e.g., low auto-fluorescing polymer etc.). Glass can be manufactured through etching and bonding processes, known to one of ordinary skill in the art. Thermoplastics can be manufactured through an embossing process or injection molding process, as well known to one of ordinary skill in the art, and is of suitable size. In certain embodiments, microfluidic chips can be manufactured from a combination of glass and thermoplastic.

Referring now to FIGS. 1-11, the present invention features microfluidic chip (100) comprising at least one flow focusing channel (120) in which from an upstream end (127) to a downstream end (128) thereof, at least a portion of the flow focusing channel (120) has a reduction in height and at least a portion of the flow focusing channel (120) narrows in width, thereby geometrically constricting the flow focusing channel (120). The geometrical constriction of the flow focusing channel (120) is configured to focus a material in a fluid that is flowing through the flow focusing channel (120).

In some embodiments, a ramp, a step, or constriction is disposed on a bottom surface (121) of the flow focusing channel (120), a top surface (122) of the flow focusing channel (120), or both, which reduces the height reduction of the portion of the flow focusing channel (120). The ramp, step, or constriction narrows the channel in the vertical or longitudinal direction. In other embodiments, the flow focusing channel (120) has a first sidewall (125) and a second sidewall (126) opposite the first sidewall (125). The sidewalls (125, 126) taper the flow focusing channel (120) to form the portion of the flow focusing channel (120) that narrows in width. The sidewalls (125, 126) are angled so that the width of the channel narrows in a horizontal or lateral direction. In some other embodiments, the narrowing effect is created by at least a portion of the flow focusing channel (120) having a shape of a cone with a larger diameter of the cone biased towards the upstream end (127) and a smaller diameter of the cone biased towards the downstream end (128).

As shown in FIGS. 4A-4F and 11, in one embodiment, the portion of the flow focusing channel (120) with the height reduction and the portion of the flow focusing channel (120) narrowing in width are sequential. In another embodiment, the portion of the flow focusing channel (120) with the height reduction and the portion of the flow focusing channel (120) narrowing in width are simultaneous, as shown in FIGS. 5-7B and 9A-9B, or overlapping, as shown in FIGS. 8A-8B and 10A-10B.

According to other embodiments, the present invention features a microfluidic chip (100) comprising a first micro-channel (110) and at least one flow focusing region (120) fluidly coupled to the first micro-channel (110). The first micro-channel (110) may include an inlet (112) through which a sample fluid enters the first micro-channel (110). The flow focusing region (120) is formed by a bottom surface (121), a top surface (122), a first sidewall (125) and a second sidewall (126) opposite the first sidewall (125). From an upstream end (127) of the flow focusing region to a downstream end (128) of the flow focusing region, at least a portion of the bottom surface (121) is raised, at least a portion of the top surface (122) is lowered, and at least a portion of the first and second sidewalls (125, 126) taper the flow focusing region (120), thereby reducing a cross-sectional area (129) of the flow focusing region at the downstream end (128) relative to the upstream end (127). The cross-sectional views in FIGS. 4A-9B illustrate this reduction in the cross-sectional area (129).

In some embodiments, the microfluidic chip may further comprise one or more sheath fluid micro-channels (130) intersecting the first micro-channel (110), which forms an intersection region (115). The one or more sheath fluid micro-channels (130) are configured to flow a sheath fluid into the intersection region (115) and into the first micro-channel (110) to cause laminar flow. It is to be understood that the one or more sheath fluid micro-channels (130) are upstream of the flow focusing region (120). In one embodiment, the device may have one sheath fluid micro-channel (130) intersecting the first micro-channel (110) at the intersection region (115) to cause laminar flow. In another embodiment, the device may have at least two sheath fluid micro-channels (130) intersecting the first micro-channel (110) at the intersection region (115) to cause laminar flow. In other embodiments, the microfluidic chip may further comprise one or more output micro-channels (140) fluidly coupled to the first micro-channel (110) downstream of the flow focusing region (120). The one or more output micro-channels (140) are configured to output fluids, which may have components such as particles or cellular material, from the first micro-channel (110).

In one embodiment, the bottom surface (121) includes a ramp (123) having a positive slope or a step that raises the portion of the bottom surface. For example, the entire bottom surface (121) may be a ramp (123) that gradually increases a height of the bottom surface from the upstream end (127) to the downstream end (128). In one embodiment, the top surface (122) includes a ramp (124) having a negative slope or a step that lowers the portion of the top surface. The ramp (124) may form the entire top surface (122) such that a height of the top surface gradually decreases from the upstream end (127) to the downstream end (128). In yet another embodiment, the entire first and second sidewalls (125, 126) are angled so as to taper the flow focusing region (120) from the upstream end (127) to the downstream end (128).

In some embodiments, at least two of the raised portion of the bottom surface (121), the lowered of the portion of the top surface (122), and the sidewall tapering occur simultaneously as shown in FIGS. 5, 7A-7B, and 9A-9B. In other embodiments, at least two of the raised portion of the bottom surface (121), the lowered portion of the top surface (122), and the sidewall tapering are overlapping as shown in FIGS. 8A-8B and 10A-10B. In yet other embodiments, the raised portion of the bottom surface (121), the lowered portion of the top surface (122), and the sidewall tapering occur in a pre-determined sequence as illustrated in FIGS. 4A-4F.

In preferred embodiments, the microfluidic chip of the present invention utilizes physical features, such as ramps, steps, constrictions, and the like, to narrow the main micro-channel (110) from a minimum of three directions, or more preferably, from all four directions. In some embodiments, the narrowing can occur simultaneous from all four directions, or the narrowing can be sequential or overlapping so that narrowing at any instantaneous point along the channel can be from a single direction or from more than one direction. In other embodiments, the narrowing at an instantaneous point upstream or downstream can be from a different direction or include a different direction in the more than one direction. Without wishing to limit the invention to a particular theory or mechanism, the focusing effect that results from a particular physical feature (e.g., a vertical ramp) is not restricted only to the immediate location in which the physical feature is present; preferably, the effect may extend up- or downstream. Accordingly, a focusing region may comprise a series of physical features that appear to be separate features, but together create a single focusing region through the overlap of the focusing effects of each feature.

In some embodiments, the amount of change in the physical features (e.g. the height of a vertical ramp or step, or the amount of tapering) can differ amongst the individual physical features in a given focusing region. For example, a bottom ramp can raise the bottom surface of the channel by 30 µm, while the ramp in the top surface of the channel lowers the top of the channel by 15 µm. Thus, the total reduction in the channel height is 45 µm, but the individual features account for different proportions of the total change.

Figure 3A:
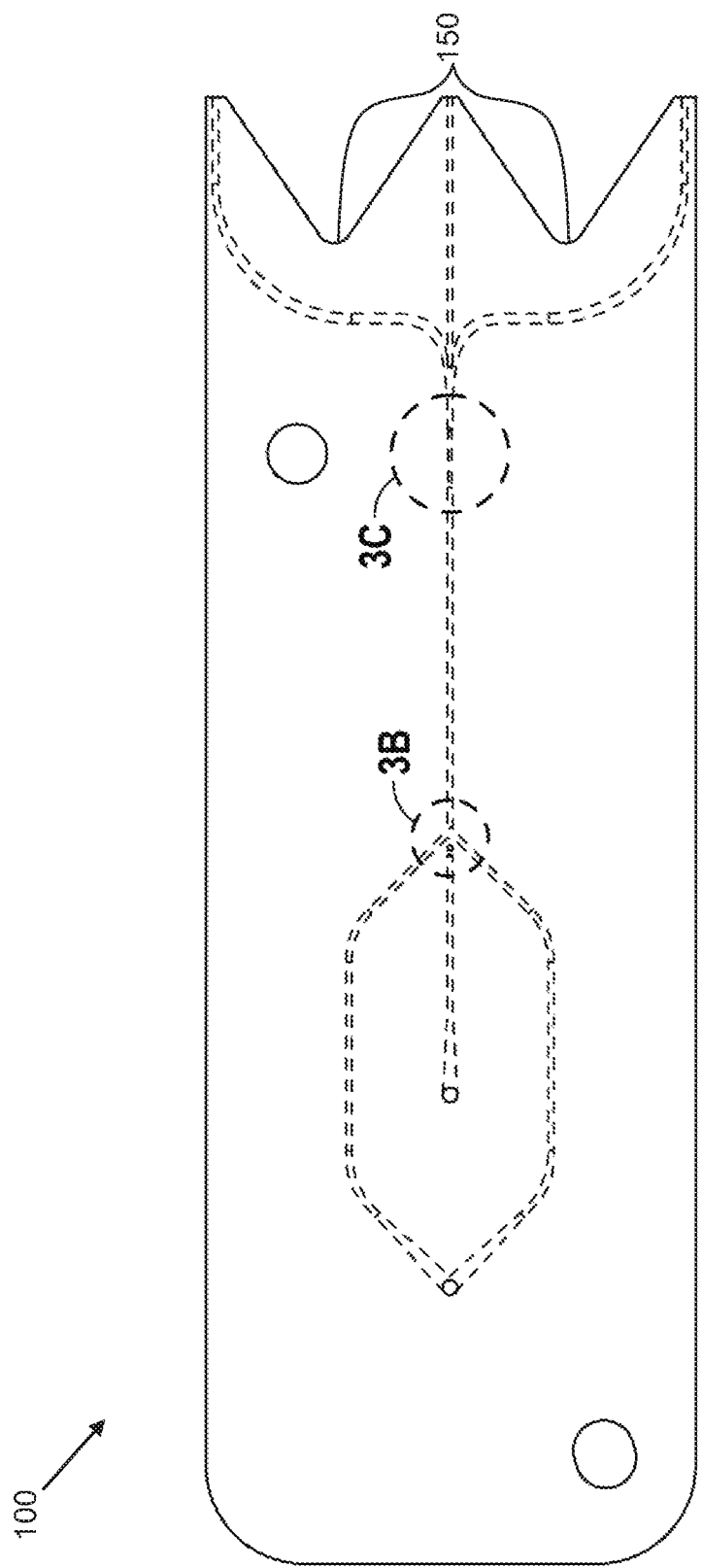
FIG. 3A shows a top view of the microfluidic device with the top later stacked atop the bottom layer.
Figure 3B:
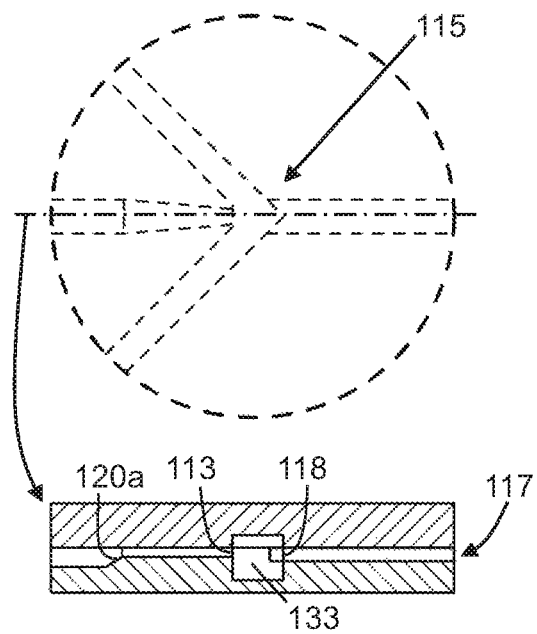
FIG. 3B shows a close-up view and a cross-sectional side view of the intersection region in the stacked layers shown in FIG. 3A.
Figure 3C:
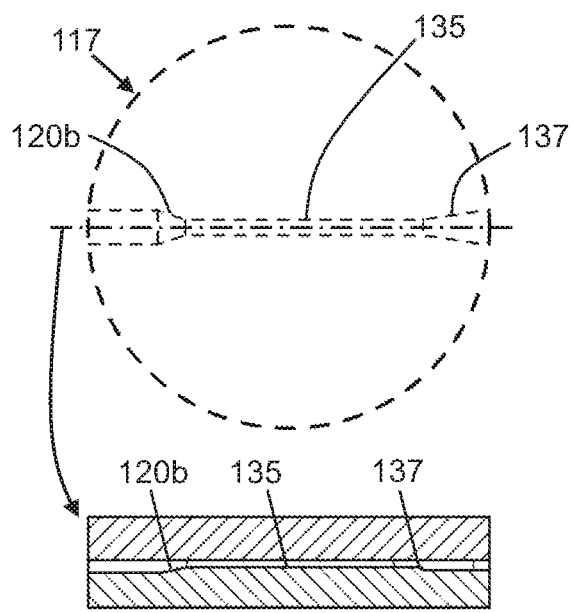
FIG. 3C shows a close-up view and a cross-sectional side view of the flow focusing region in the stacked layers shown in FIG. 3A.
Figure 3D:
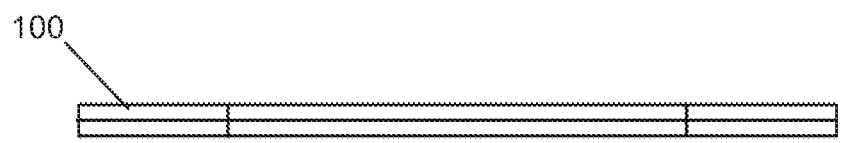
FIG. 3D is a side view of the stacked layers of the microfluidic device in FIG. 3A.
Figure 4A:
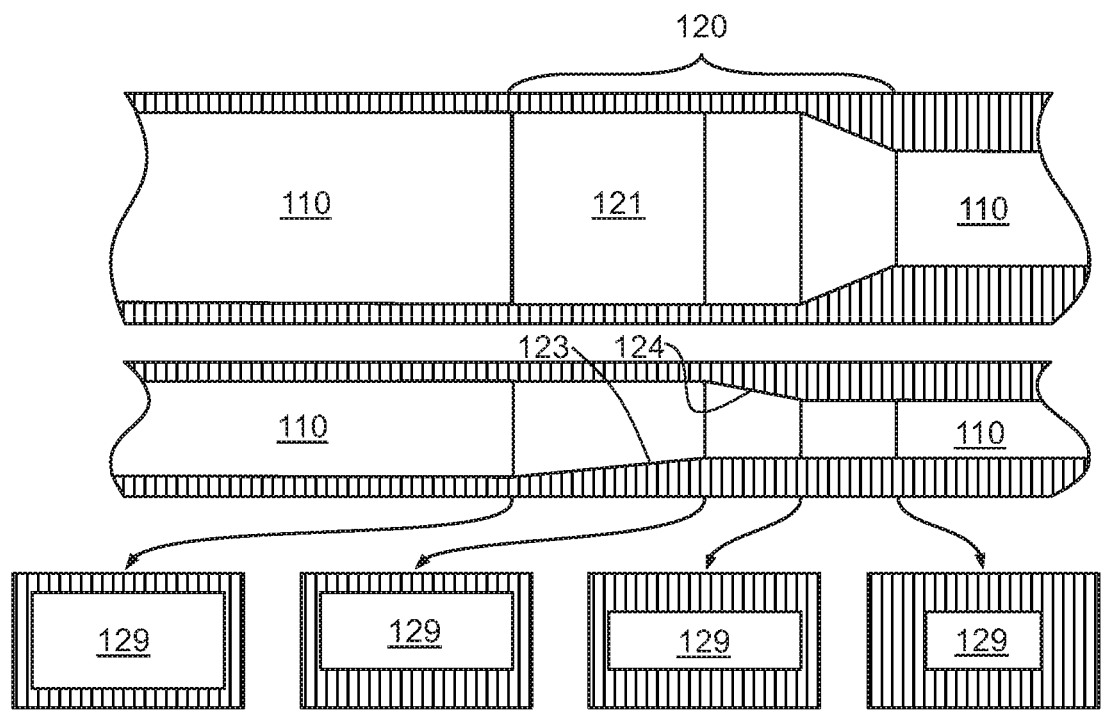
Figure 4B:
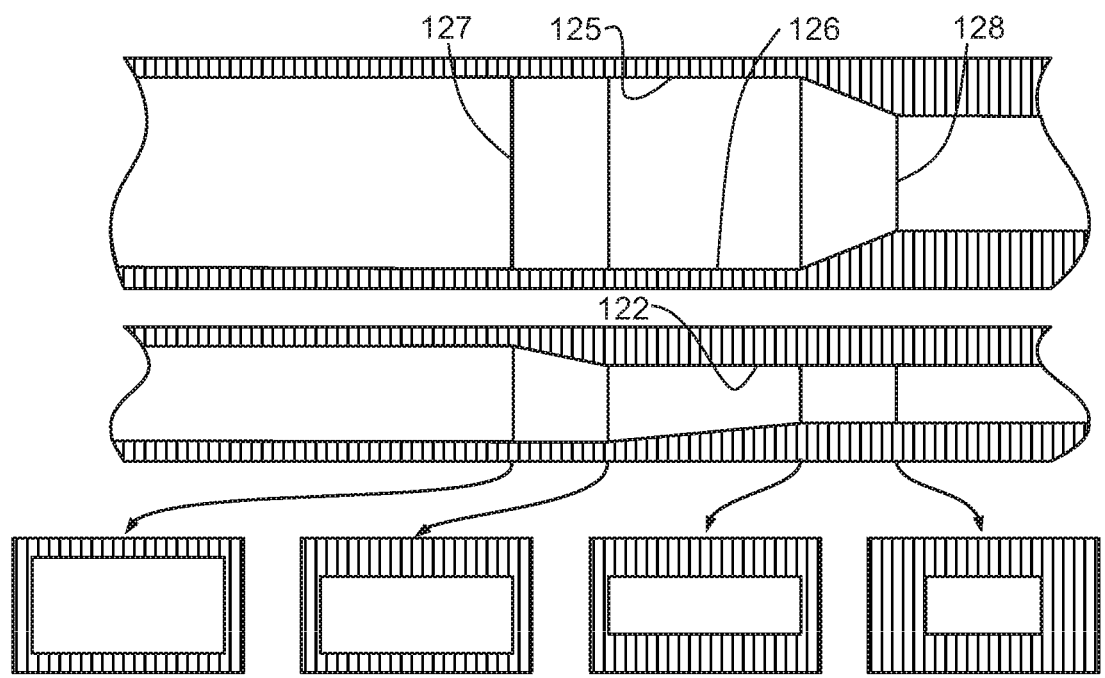
Figure 4C:
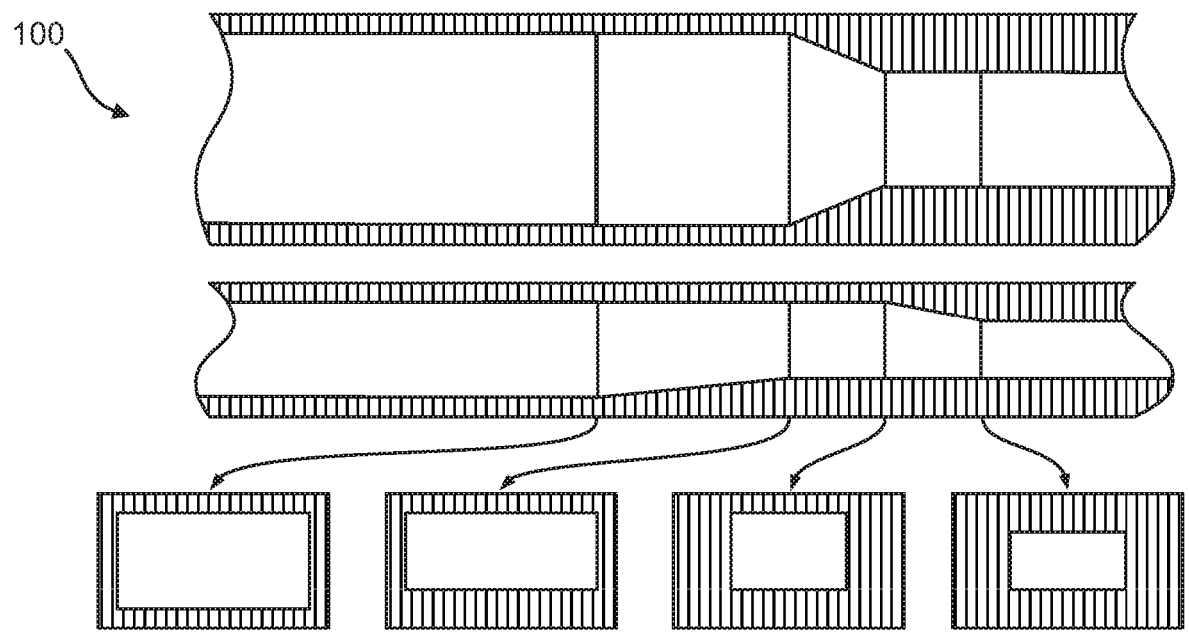
Figure 4D:
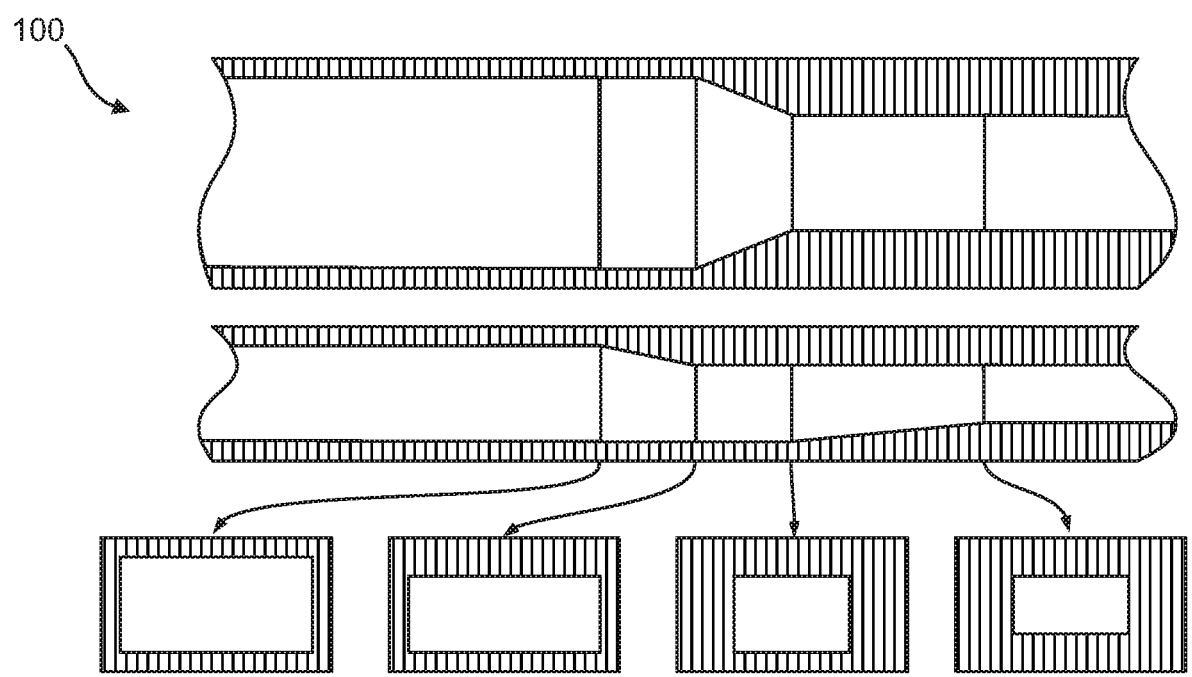
Figure 4E:
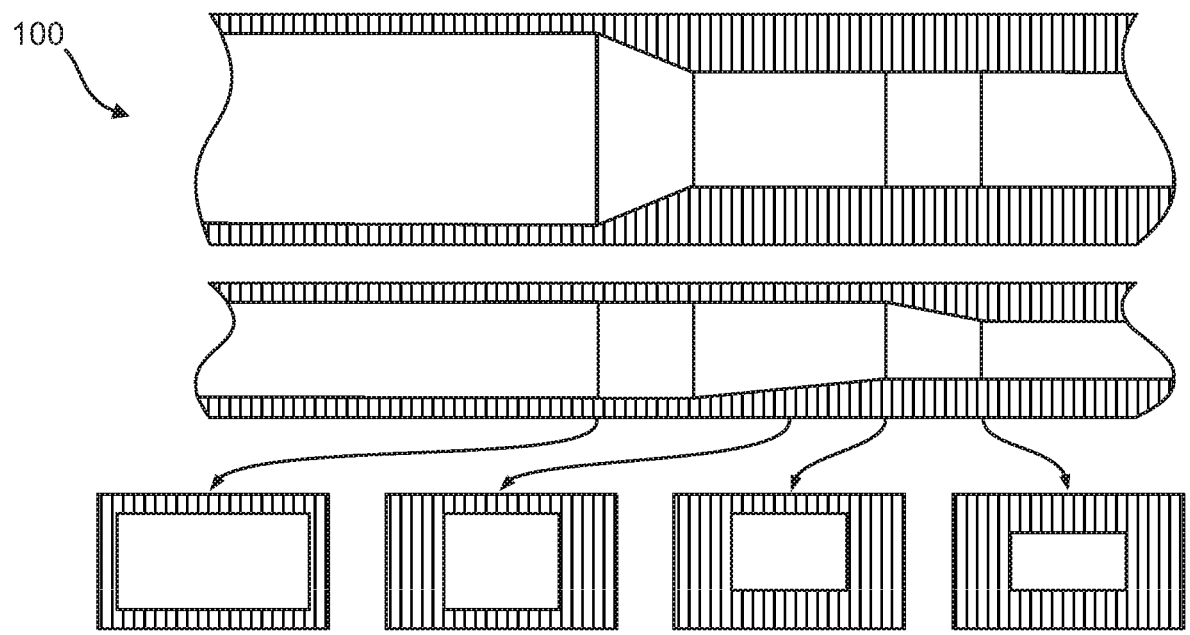
Figure 4F:
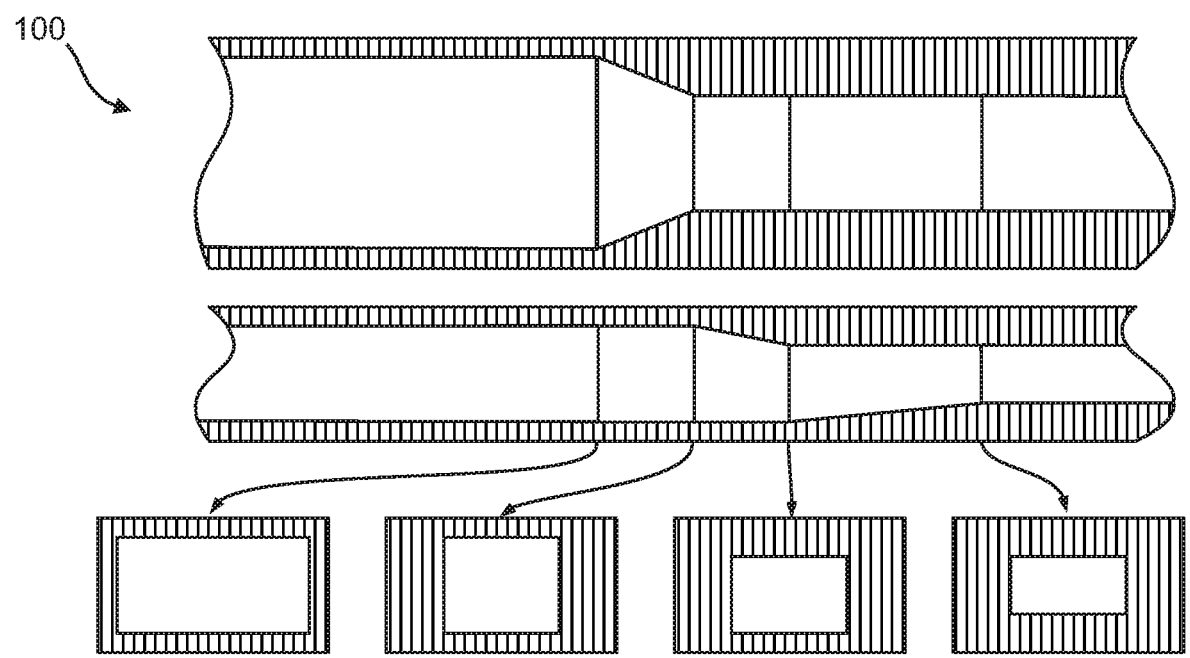

As shown in FIG. 3D, the microfluidic chip may include two or more structural layers in which are disposed micro-channels that can serve as a sample input channel, a sheath or buffer fluid channel, or an output channel, etc. However, one of ordinary skill in the art would know that less or additional layers may be used, and the channels may be disposed in any of the layers as long as the object of the present invention is achieved. The micro-channels are of suitable size to accommodate a particulate laminar flow, and may be disposed in any of the layers of the chip in the appropriate length, as long as the object of the present invention is realized. The desired flow rate through the microfluidic chip may be controlled by a predetermined introduction flow rate into the chip, maintaining the appropriate micro-channel dimensions within the chip, by pumping mechanisms, providing narrowing of the micro-channels at various locations, and/or by providing obstacles or dividers within the micro-channels.

A plurality of inputs is provided into the microfluidic chip, which provides access to the micro-channels. In one embodiment, a sample input is used for introducing components in a sample fluid mixture into a sample input channel from a reservoir source. The microfluidic chip also includes a sheath/buffer input for the introduction of a sheath or buffer fluid. Sheath or buffer fluids are well known in the art of microfluidics, and in one embodiment, may contain nutrients well known in the art to maintain the viability of the components (i.e., sperm cells) in the fluid mixture.

In one embodiment, one or more of output channels (140) fluidly coupled to the main micro-channel (110) are provided for removal of fluid which has flowed through the microfluidic chip, including isolated fluid components and/or sheath or buffer fluids. As shown in FIG. 3, one embodiment of the device may comprise three output channels (140), which include two side output channels and a center output channel disposed between said side channels. Each channel (140) may have its own output; however, the number of outputs may be less or more depending on the number of components to be isolated from the fluid mixture. In some embodiments, instead of a straight edge, where necessary, one or more notches or recesses (150) are disposed at an edge of the microfluidic chip to separate the outputs and for attachment of external tubing etc. For example, the chip may have notches (150) that create a "W" shaped edge at the output.

In one embodiment, the sample fluid mixture including the components is introduced into the sample input (112), and the fluid mixture flows through the main channel (110). The sheath or buffer fluids are introduced into the sheath/buffer channels (130), and flow into the main channel (110) to join with the fluid mixture at the intersection region (115). The sheath or buffer fluids and the fluid mixture undergo laminar flow towards the flow focusing region (120) before flowing out through the one or more output channels (140). In some embodiments, the micro-channels of the microfluidic chip may be dimensioned so as to achieve a desired flow rate(s) that meets the objective of the present invention. In one embodiment, the micro-channels may have substantially the same dimensions, however, one of ordinary skill in the art would know that the size of any or all of the channels in the microfluidic chip may vary in dimension (i.e., between 50 and 500 microns), as long as the desired flow rate(s) is achieved.

In another embodiment, as shown in FIG. 2B, the main channel (110) may taper at the entry point into the intersection region (115) to control and speed up the flow into the intersection, and allow the sheath or buffer fluids from the sheath micro-channels (130) to compress the sample fluid mixture in a first direction (i.e., horizontally) on at least two sides. For example, the sheath or buffer fluids from the sheath micro-channels (130) intersect the main micro-channel (110) at a substantially perpendicular angle or less, such as an angle of 45°, thereby compressing the fluid mixture flow such that the components in the fluid mixture are compressed or flattened, and oriented in the selected or desired direction. Thus, the sample fluid mixture becomes a relatively smaller, narrower stream, bounded or surrounded by sheath or buffer fluids, while maintaining laminar flow in the main micro-channel (110). However, one of ordinary skill in the art would appreciate that the depicted configurations, angles, and structural arrangements of the microfluidic chip layers and channels may be different as long as they achieve the desired features of the present invention.

In some embodiments, downstream from the flow focusing region (120), the components in the fluid mixture flow through the main micro-channel (110) into an interrogation apparatus where the components are interrogated and identified. In one embodiment, the interrogation apparatus includes a chamber with an opening or window cut into the microfluidic chip. The opening or window can receive a covering to enclose the interrogation chamber. The covering may be made of any material with the desired transmission requirements, such as plastic, glass, or may even be a lens. In one embodiment, the window and covering allow the components of the fluid mixture flowing in the main micro-channel (110) through the interrogation chamber to be viewed, and acted upon by a suitable radiation source configured to emit a high intensity beam with any wavelength that matches the excitation of the components.

Although a laser may be used, it is understood that any suitable other radiation sources may be used, such as a light emitting diode (LED), arc lamp, etc. to emit a beam which excites the components. In another embodiment, the light beam can be delivered to the components by an optical fiber that is embedded in the microfluidic chip at the opening.

In some embodiments, a high intensity laser beam from a suitable laser of a preselected wavelength—such as a 355 nm continuous wave (CW) (or quasi-CW) laser—is required to excite the components in the fluid mixture (i.e., sperm cells). The laser emits a laser beam through the window so as to illuminate the components flowing through the main micro-channel (110) in the interrogation region of the chip. Since the laser beam can vary in intensity widthwise along the main micro-channel, with the highest intensity generally at the center of the main micro-channel (e.g., midsection of the main channel width) and decreasing therefrom, it is imperative that the flow focusing region focuses the sperm cells at or near the center of the fluid stream where optimal illumination occurs at or near the center of the illumination laser spot. Without wishing to be bound to a particular belief, this can improve accuracy of the interrogation and identification process In some embodiments, the high intensity beam interacts with the components such that the emitted light, which is induced by the beam, is received by an objective lens. The objective lens may be disposed in any suitable position with respect to the microfluidic chip. In one embodiment, the emitted light received by the objective lens is converted into an electronic signal by an optical sensor, such as a photomultiplier tube (PMT) or photodiode, etc. The electronic signal can be digitized by an analog-to-digital converter (ADC) and sent to a digital signal processor (DSP) based controller. The DSP based controller monitors the electronic signal and may then trigger a sorting mechanism.

In other embodiments, the interrogation apparatus may comprise a detector such as a photomultiplier tube (PMT), an avalanche photodiode (APD), or a silicon photomultiplier (SiPM). For example, the optical sensor of the interrogation apparatus may be APD, which is a photodiode with substantial internal signal amplification through an avalanche process.

In some embodiments, a piezoelectric actuator assembly may be used to sort the desired components in the fluid mixture in main micro-channel (110) as the components leave the interrogation area after interrogation. A trigger signal sent to the piezoelectric actuator is determined by the sensor raw signal to activate a particular piezoelectric actuator assembly when the selected component is detected. In some embodiments, a flexible diaphragm made from a suitable material, such as one of stainless steel, brass, titanium, nickel alloy, polymer, or other suitable material with desired elastic response, is used in conjunction with an actuator to push target components in the main micro-channel into an output channel (140) to isolate the target components from the fluid mixture. The actuator may be a piezoelectric, magnetic, electrostatic, hydraulic, or pneumatic type actuator.

In alternative embodiments, a piezoelectric actuator assembly or a suitable pumping system may be used to pump the sample fluid into the main micro-channel (110) toward the intersection region (115). The sample piezoelectric actuator assembly would be disposed at sample input (112). By pumping the sample fluid mixture into the main micro-channel, a measure of control can be made over the spacing of the components therein, such that a more controlled relationship may be made between the components as they enter the main micro-channel (110).

Other embodiments of sorting or separating mechanisms that may be used in accordance with the present invention include, but are not limited to, droplet sorters, mechanical separation, fluid switching, acoustic focusing, holographic trapping/steering, and photonic pressure/steering. In a preferred embodiment, the sorting mechanism for sex-sorting of sperm cells comprises laser kill/ablation of selected X-chromosome-bearing sperm cells.

In laser ablation, the laser is activated when an X-chromosome-bearing sperm cell is detected during interrogation. The laser emits a high intensity beam directed at the X-chromosome-bearing sperm cell centered within the fluid stream. The high intensity beam is configured to cause DNA and/or membrane damage to the cell, thereby causing infertility or killing the X-chromosome-bearing sperm cell. As a result, the final product is comprised predominantly of Y-chromosome-bearing sperm cells. In preferred embodiments, the reduction in the cross-sectional area (129) of the flow focusing region geometrically compresses the fluid that carries sperm cells. The geometric compression of the fluid centralizes the sperm cells within the fluid such that the sperm cells are focused at or near a center of the first micro-channel (110). Since the laser beam varies in intensity widthwise along the main micro-channel, with the highest intensity generally at the center of main micro-channel and decreasing therefrom, it is imperative that the flow focusing region focuses the sperm cells at or near the center of the fluid stream where the laser beam has the highest intensity to impart maximum damage to the selected sperm cells.

Chip Operation

In one embodiment, as previously stated, the components that are to be isolated include, for example: isolating viable and motile sperm from non-viable or non-motile sperm; isolating sperm by gender, and other sex sorting variations; isolating stems cells from cells in a population; isolating one or more labeled cells from un-labeled cells distinguishing desirable/undesirable traits; sperm cells with different desirable characteristics; isolating genes in nuclear DNA according to a specified characteristic; isolating cells based on surface markers; isolating cells based on membrane integrity (viability), potential or predicted reproductive status (fertility), ability to survive freezing, etc.; isolating cells from contaminants or debris; isolating healthy cells from damaged cells (i.e., cancerous cells) (as in bone marrow extractions); red blood cells from white blood cells and platelets in a plasma mixture; and isolating any cells from any other cellular components, into corresponding fractions; damaged cells, or contaminants or debris, or any other biological materials that are desired to isolated. The components 160 may be cells or beads treated or coated with, linker molecules, or embedded with a fluorescent or luminescent label molecule(s). The components may have a variety of physical or chemical attributes, such as size, shape, materials, texture, etc.

In one embodiment, a heterogeneous population of components may be measured simultaneously, with each component being examined for different quantities or regimes in similar quantities (e.g., multiplexed measurements), or the components may be examined and distinguished based on a label (e.g., fluorescent), image (due to size, shape, different absorption, scattering, fluorescence, luminescence characteristics, fluorescence or luminescence emission profiles, fluorescent or luminescent decay lifetime), and/or particle position etc.

In one embodiment, a two-step focusing method may be used in order to position the components in the main micro-channel (110) for interrogation in the interrogation chamber. The first focusing step of the present invention is accomplished by inputting a fluid sample containing components, such as sperm cells etc., through sample input (112), and inputting sheath or buffer fluids through the sheath or buffer micro-channels (130). In some embodiments, the components are pre-stained with dye (e.g., Hoechst dye), in order to allow fluorescence, and for imaging to be detected. Initially, the components in the sample fluid mixture flow through micro-channel (110) and have random orientation and position. At the intersection region (115), the sample mixture flowing in the micro-channel (110) is compressed by the sheath or buffer fluids flowing from the sheath or buffer micro-channels (130), in a first direction (e.g., at least horizontally on at least both sides of the flow, if not all sides depending on where the main micro-channel (110) enters the intersection region (115)), when the sheath or buffer fluids meet with the sample mixture. As a result, the components are focused and compressed into a thin stream and the components (e.g., sperm cells) move toward a center of the channel width.

In preferred embodiments, the present invention includes a second focusing step where the sample mixture containing the components is further compressed in the flow focusing region (120) using physical or geometric compression, instead of a second intersection of sheath fluids. Thus, with the second focusing step of the present invention, the sample stream is focused at the center of the channel, and the components flow along the center of the channel in approximately a single file formation. Without wishing to be bound to a particular theory or mechanism, the physical/geometric compression has the advantage of reducing the volume of sheath fluid since the second intersection of sheath fluids is eliminated.

Accordingly, the microfluidic devices described herein may be used in the two-step focusing method described above. In one embodiment, the present invention provides a method of focusing particles in a fluid flow. The method may comprise providing any one of the microfluidic devices described herein, flowing a fluid mixture comprising the particles into the sample micro-channel (110), flowing a sheath fluid through one or more sheath fluid channels (130) into a first focusing region such that the sheath fluid compresses the fluid mixture from at least one side while maintaining laminar flow in the sample micro-channel (110), and flowing the fluid mixture and sheath fluid through a second focusing region (120) comprising physical structures. The second focusing region (120) does not include the introduction of additional sheath fluid. Compression of the fluid mixture, by the introduction of sheath fluid and/or by physical structures at the first focusing region constricts the particles of the fluid mixture into a relatively smaller, narrower stream bounded by the sheath fluids. For example, sheath fluid introduced into the sample micro-channel (110) by two sheath fluid channels (130) can compress the fluid mixture stream from two sides into a relatively smaller, narrower stream while maintaining laminar flow. Flow of the fluid mixture and sheath fluids in the second focusing region causes further constriction of the fluid mixture stream and re-orienting of the particles within the stream, which is caused by the physical structures such as the raised portion of the bottom surface (121), the lowered portion of the top surface (122), and the tapering portions of the first and second sidewall (125, 126), thus focusing the particles.

In some embodiments, the components of the sample are sperm cells, and because of their pancake-type or flattened teardrop shaped head, the sperm cells can re-orient themselves in a predetermined direction as they undergo the focusing step—i.e., with their flat surfaces perpendicular to the direction of a light beam. Thus, the sperm cells develop a preference on their body orientation while passing through the two-step focusing process. Specifically, the sperm cells tend to be more stable with their flat bodies perpendicular to the direction of the compression. Hence, with the control of the sheath or buffer fluids, the sperm cells which start with random orientation, now achieve uniform orientation. Thus, the sperm cells not only make a single file formation at the center of the channel, but they also achieve a uniform orientation. Thus, the components introduced into sample input, which may be other types of cells or other materials as previously described, undergo the two-step focusing steps, which allow the components to move through the main micro-channel (110) in a single file formation, and in a more uniform orientation (depending on the type of components), which allows for easier interrogation of the components.

In conjunction with the preceding embodiment, the present invention also provides a method of producing a fluid with gender-skewed sperm cells implementing the two-step focusing procedure. Referring to FIG. 12, the method may comprise providing any one of the microfluidic devices described herein, flowing a semen fluid comprising sperm cells into the sample micro-channel (110), flowing a sheath fluid through the one or more sheath fluid channels (130) such that the sheath fluid compresses the semen fluid from at least one side while maintaining laminar flow in the sample micro-channel (110), thereby constricting the semen fluid into a relatively smaller, narrower stream, flowing the semen fluid and sheath fluids into the focusing region (120) to further constrict the semen fluid and centralize the sperm cells within the stream, without that addition of additional sheath fluid, such that the sperm cells are focused at or near a center of the sample micro-channel (110), determining a chromosome type of the sperm cells in the focused stream, and sorting Y-chromosome-bearing sperm cells from X-chromosome-bearing sperm cells, thereby producing the fluid comprising gender-skewed sperm cells that are predominantly Y-chromosome-bearing sperm cells.

In some embodiments, the chromosome type of the sperm cells may be determined using any one of the interrogation apparatus described herein. In one embodiment, the interrogation apparatus is disposed downstream from the focusing region (120). The interrogation apparatus may comprise a radiation source that illuminates and excites the sperm cells, and a response of the sperm cell is indicative of the chromosome type in the sperm cell. In preferred embodiment, the Y-chromosome-bearing sperm cells are sorted from the X-chromosome-bearing sperm cells by laser ablation, which exposes the cells to a high intensity laser source that damages or kills cells that are determined to bear an X-chromosome. In one embodiment, the gender-skewed sperm cells are comprised of at least 55% of Y-chromosome-bearing sperm cells. In another embodiment, the gender-skewed sperm cells are comprised of about 55%-99% of Y-chromosome-bearing sperm cells. In yet another embodiment, the gender-skewed sperm cells are comprised of at least 99% of Y-chromosome-bearing sperm cells.

In one embodiment, further downstream in the microchannel (110), the components are detected in the interrogation chamber using a radiation source. The radiation source emits a light beam (which may be via an optical fiber) which is focused at the center of the channel widthwise. In one embodiment, the components, such as sperm cells, are oriented by the focusing region such that the flat surfaces of the components are facing toward the beam. In addition, all components are preferably aligned in a single file formation by focusing as they pass under a radiation source. As the components pass under the radiation source and are acted upon by a light beam, the components emit the fluorescence which indicates the desired components. For example, with respect to sperm cells, X chromosome cells fluoresce at a different intensity from Y chromosome cells; or cells carrying one trait may fluoresce in a different intensity or wavelength from cells carrying a different set of traits. In addition, the components can be viewed for shape, size, or any other distinguishing indicators.

In one embodiment, interrogation of the sample containing components (i.e., biological material), is accomplished by other methods. Overall, methods for interrogation may include direct visual imaging, such as with a camera, and may utilize direct bright-light imaging or fluorescent imaging; or, more sophisticated techniques may be used such as spectroscopy, transmission spectroscopy, spectral imaging, or scattering such as dynamic light scattering or diffusive wave spectroscopy. In some cases, the optical interrogation region may be used in conjunction with additives, such as chemicals which bind to or affect components of the sample mixture or beads which are functionalized to bind and/or fluoresce in the presence of certain materials or diseases.

These techniques may be used to measure cell concentrations, to detect disease, or to detect other parameters which characterize the components.

However, in another embodiment, if fluorescence is not used, then polarized light back scattering methods may also be used. Using spectroscopic methods, the components are interrogated and the spectrum of those components which had positive results and fluoresced (i.e., those components which reacted with a label) are identified for separation. In some embodiments, the components may be identified based on the reaction or binding of the components with additives or sheath or buffer fluids, or by using the natural fluorescence of the components, or the fluorescence of a substance associated with the component, as an identity tag or background tag, or met a selected size, dimension, or surface feature, etc., are selected for separation. In one embodiment, upon completion of an assay, selection may be made, via computer and/or operator, of which components to discard and which to collect.

Continuing with the embodiment of beam-induced fluorescence, the emitted light beam is then collected by the objective lens, and subsequently converted to an electronic signal by the optical sensor. The electronic signal is then digitized by an analog-digital converter (ADC) and sent to an electronic controller for signal processing. The electronic controller can be any electronic processer with adequate processing power, such as a DSP, a Micro Controller Unit (MCU), a Field Programmable Gate Array (FPGA), or even a Central Processing Unit (CPU). In one embodiment, the DSP-based controller monitors the electronic signal and may then trigger a sorting mechanism when a desired component is detected. In another embodiment, the FPGA-based controller monitors the electronic signal and then either communicates with the DSP controller or acts independently to trigger a sorting mechanism when a desired component is detected. In some other embodiments, the optical sensor may be a photomultiplier tube (PMT), an avalanche photodiode (APD), or a silicon photomultiplier (SiPM). In a preferred embodiment, the optical sensor may be an APD that detects the response of the sperm cell to interrogation.

In one embodiment of the sorting mechanism, the selected or desired components in the main micro-channel (110) in the interrogation chamber are isolated into a desired output channel using a piezoelectric actuator. In an exemplary embodiment, the electronic signal activates the driver to trigger the actuator at the moment when the target or selected component arrives at a cross-section point of jet channels and the main micro-channel (110). This causes the actuator to contact a diaphragm and push it, compressing a jet chamber, and squeezing a strong jet of buffer or sheath fluids into the main micro-channel (110), which pushes the selected or desired component into a desired output channel.

In some embodiments, the isolated components are collected from their respective output channel (140) for storing, further separation, or processing, such as cryopreservation. In some embodiments, the outputted components may be characterized electronically, to detect concentrations of components, pH measuring, cell counts, electrolyte concentration, etc.

Chip Cassette and Holder

In some embodiments, the microfluidic chip may be loaded on a chip cassette, which is mounted on chip holder. The chip holder is mounted to a translation stage to allow fine positioning of the holder. For instance, the microfluidic chip holder is configured to hold the microfluidic chip in a pre-determined position such that the interrogating light beam intercepts the fluid components. In one embodiment, the microfluidic chip holder is made of a suitable material, such as aluminum alloy, or other suitable metallic/polymer material. A main body of the holder may be any suitable shape, but its configuration depends on the layout of the chip. In further embodiments, the main body of the holder is configured to receive and engage with external tubing for communicating fluids/samples to the microfluidic chip. A gasket of any desired shape, or O-rings, may be provided to maintain a tight seal between the microfluidic chip and the microfluidic chip holder. The gasket may be a single sheet or a plurality of components, in any configuration, or material (i.e., rubber, silicone, etc.) as desired. In one embodiment, the gasket interfaces, or is bonded (using an epoxy) with a layer of the microfluidic chip. The gasket is configured to assist in sealing, as well as stabilizing or balancing the microfluidic chip in the microfluidic chip holder. The details of the cassette and holder and the mechanisms for attachment of the chip to the cassette and holder, are not described in any detail, as one of ordinary skill in the art would know that these devices are well-known and may be of any configuration to accommodate the microfluidic chip, as long as the objectives of the present invention are met.

In some embodiments, a pumping mechanism includes a system having a pressurized gas which provides pressure for pumping sample fluid mixture from reservoir (i.e., sample tube) into sample input of the chip. In other embodiments, a collapsible container having sheath or buffer fluid therein, is disposed in a pressurized vessel, and the pressurized gas pushes fluid such that fluid is delivered via tubing to the sheath or buffer input of the chip.

In one embodiment, a pressure regulator regulates the pressure of gas within the reservoir, and another pressure regulator regulates the pressure of gas within the vessel. A mass flow regulator controls the fluid pumped via tubing, respectively, into the sheath or buffer input. Thus, tubing is used in the initial loading of the fluids into the chip, and may be used throughout the chip to load a sample fluid into sample input.

In accordance with the present invention, any of the operations, steps, control options, etc. may be implemented by instructions that are stored on a computer-readable medium such as a memory, database, etc. Upon execution of the instructions stored on the computer-readable medium, for example, by a computing device or processor, the instructions can cause the computing device or processor to perform any of the operations, steps, control options, etc. described herein. In some embodiments the operations described in this specification may be implemented as operations performed by a data processing apparatus or processing circuit on data stored on one or more computer-readable storage devices or received from other sources. A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A program can be stored in a portion of a file that holds other programs or data, in a single file dedicated to the program in question, or in multiple coordinated files. A program can be deployed to be executed on one computer or on multiple computers interconnected by a communication network. Processing circuits suitable for the execution of a computer program include, by way of example, both general and special purpose microprocessors, and any one or more processors of any kind of digital computer.

In one embodiment, a user interface of the computer system includes a computer screen which displays the components in a field of view acquired by a CCD camera over the microfluidic chip. In another embodiment, the computer controls any external devices such as pumps, if used, to pump any sample fluids, sheath or buffer fluids into the microfluidic chip, and also controls any heating devices which set the temperature of the fluids being inputted into the microfluidic chip.

It should be noted that the orientation of various elements may differ according to other illustrative embodiments, and that such variations are intended to be encompassed by the present disclosure. The construction and arrangements of the microfluidic chip, as shown in the various illustrative embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various illustrative embodiments without departing from the scope of the present disclosure.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A microfluidic chip (100) comprising:
    a. a sample micro-channel (110), wherein the sample micro-channel (110) includes a narrowing region (120a) downstream of an inlet (112) of the sample micro-channel, wherein the narrowing region (120a) comprises:
        i. an upstream constricting portion having a positively sloping bottom surface that reduces a height of the narrowing region (120a); and
        ii. a downstream constricting portion having sidewalls that taper to reduce a width of the narrowing region (120a),
            wherein the upstream constricting portion and the downstream constricting portion geometrically constricts the narrowing region (120a);
    b. two sheath fluid micro-channels (130) intersecting the sample micro-channel (110) to form an intersection region (115); and
    c. a downstream micro-channel (117) fluidly connected to the intersection region (115), comprising:
        i. a flow focusing region (120b) comprising a positively sloping bottom surface and sidewalls that taper to reduce a height of the downstream micro-channel and a width of the downstream micro-channel simultaneously, thereby reducing a cross-sectional area of the downstream micro-channel;
        ii. an interrogation region (135) downstream of the flow focusing region (120b); and
        iii. an expansion region (137) downstream of the interrogation region (135), comprising:
            A. an expansion portion having sidewalls that widen to increase a width of the downstream micro-channel; and
            B. a negatively sloping bottom surface that increases the height of the downstream micro-channel;
        wherein an outlet (113) of the sample micro-channel is positioned at or near mid-height of an outlet (133) of each of the two sheath fluid micro-channels,
        wherein an inlet (118) of the downstream micro-channel is positioned at or near mid-height of the outlet (133) of each of the two sheath fluid micro-channels,
        wherein the sample micro-channel (110) is configured to flow a sample fluid mixture, wherein the two sheath fluid micro-channels (130) are each configured to flow a sheath fluid into the intersection region (115) to cause laminar flow and to compress the sample fluid mixture flowing from the sample micro-channel (110) at least horizontally from at least two sides such that the sample fluid mixture becomes surrounded by sheath fluid and compressed into a thin stream.

2. The microfluidic chip (100) of claim 1, wherein the intersection region (115) and the flow focusing region (120b) are configured to focus a material in the sample fluid mixture.

3. The microfluidic chip (100) of claim 2, wherein compression of the sample fluid mixture centralizes the material within the sample fluid mixture such that the material is focused at or near a center of the downstream micro-channel.

4. The microfluidic chip (100) of claim 1 further comprising a plurality of output micro-channels (140) fluidly coupled to an outlet (119) of the downstream micro-channel.

5. The microfluidic chip (100) of claim 4, wherein the plurality of output micro-channels (140) comprises two side output channels and a central output channel disposed between said side output channels.

* * * * *